United States Patent [19]

Boswell et al.

[11] Patent Number: 5,424,450
[45] Date of Patent: Jun. 13, 1995

[54] ANGIOTENSIN II RECEPTOR BLOCKING IMIDAZOLINONE DERIVATIVES

[75] Inventors: George A. Boswell; Indawati De Lucca, both of Wilmington; Mimi L. Quan, Newark, all of Del.

[73] Assignee: E. I. Du Pont de Nemours and Company, Wilmington, Del.

[21] Appl. No.: 77,145

[22] Filed: Jun. 16, 1993

Related U.S. Application Data

[63] Continuation-in-part of Ser. No. 929,454, Aug. 14, 1992, abandoned, which is a continuation-in-part of Ser. No. 747,023, Aug. 19, 1991, abandoned.

[51] Int. Cl.⁶ .................. C07D 403/10; C07D 233/36; A61K 31/41; A61K 31/415
[52] U.S. Cl. .................. 548/253; 548/321.5; 548/323.5; 548/324.5; 548/325.1
[58] Field of Search ............... 548/253, 321.5, 323.5, 548/324.5, 325.1; 514/381, 399

Primary Examiner—David B. Springer

[57] ABSTRACT

Novel imidazolinone derivatives of formula (I), which are useful as angiotensin II antagonists, are disclosed:

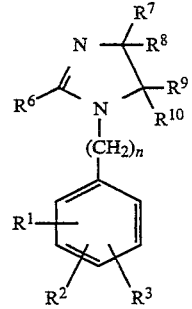

5 Claims, No Drawings

ANGIOTENSIN II RECEPTOR BLOCKING IMIDAZOLINONE DERIVATIVES

CROSS-REFERENCE TO RELATED APPLICATION

This application is a continuation-in-part of application Ser. No. 07/929,454, filed Aug. 14, 1992, which is a continuation-in-part of application Ser. No. 07/747,023, filed Aug. 19, 1991, both abandoned.

FIELD OF THE INVENTION

This invention relates to novel substituted imidazolinone derivatives. The invention also relates to pharmaceutical compositions containing the novel imidazolinone derivatives and pharmaceutical methods using them, alone and in conjugation with other drugs.

The compounds of this invention inhibit the action of the hormone angiotensin II (AII) and are useful therefore in alleviating angiotensin induced hypertension. The enzyme renin acts on a blood plasma $\alpha$2-globulin, angiotensinogen, to produce angiotensin I, which is then converted by ACE to AII. The latter substance is a powerful vasopressor agent which has been implicated as a causative agent for producing high blood pressure in various mammalian species, such as the rat, dog, and man. The compounds of this invention inhibit the action of AII at its receptors on target cells and thus prevent the increase in blood pressure produced by this hormone-receptor interaction. By administering a compound of this invention to a species of mammal with hypertension due to AII, the blood pressure is reduced. The compounds of this invention are also useful for the treatment of congestive heart failure. Administration of a compound of this invention with a diuretic such as furosemide or hydrochlorothiazide, either as a stepwise combined therapy (diuretic first) or as a physical mixture, enhances the antihypertensive effect of the compound. Administration of a compound of this invention with a NSAID can prevent renal failure which sometimcheme es results from administration of a NSAID.

Several peptide analogs of AII are known to inhibit the effects of this hormone by competitively blocking the receptors, but their experimental and clinical applications have been limited by the partial agonist activity and lack of oral absorption (M. Antonaccio, *Clin. Exp. Hypertens.*, 1982, A4, 27–346; D. H. P. Streeten and G. H. Anderson, Jr., *Handbook of Hypertension, Clinical Pharmacology of Antihypertensive Drugs*, ed., A. E. Doyle, Vol. 5, pp. 246–271, Elsevier Science Publisher, Amsterdam, The Netherlands, 1984).

Several non-peptide antagonists of AII have been disclosed. These compounds are covered by U.S. Pat. Nos. 4,207,324; 4,340,598; 4,576,958; 4,582,847; and 4,880,804; in European Patent Applications 028,834; 245,637; 253,310; and 291,969; and in articles by A. T. Chiu, et al. (*Eur. J. Pharm. Exp. Therap.*, 1988, 157, 13–21) and by P. C. Wong, et al. (*J. Pharm. Exp. Therap*, 1988, 247, 1–7). All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]pyridine-6-carboxylic acid and analogs thereof as antihypertensive agents, specifically $Ca^{2+}$ channel blockers.

L. Chang et al., in EP O 412 594 A (filed Jul. 23, 1990) disclose substituted triazolinones, triazolinethiones, and triazolinimines of the formula:

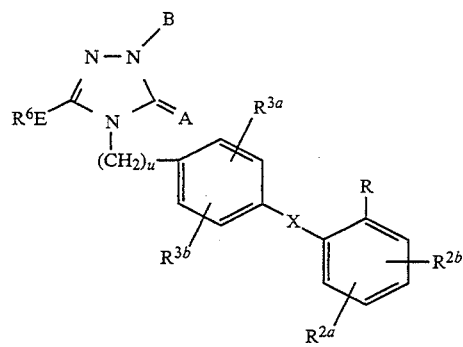

These are claimed to be antagonists of AII which are useful for treating hypertension, congestive heart failure (CHF), and elevated intraocular pressure.

C. Bernhart et al., in WO 91/14679 (published Oct. 3, 1991) disclose heterocyclic N-substituted derivatives of the formula

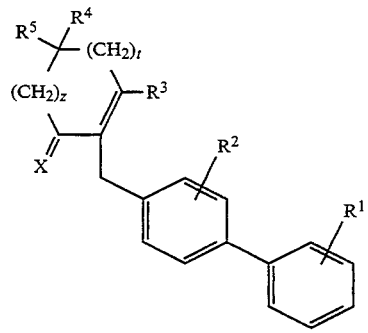

These compounds are disclosed to be antagonists of AII which are useful for treating cardiovascular disorders such as hypertension.

F. Ostermeyer et al., in EP 475,898 (published Mar. 18, 1992) disclose heterocyclic N-substituted derivatives of formula

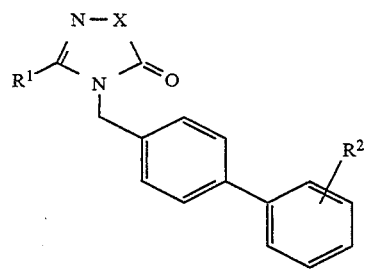

These compounds are disclosed to be antagonists of AII which are useful for treating cardiovascular disorders such as hypertension.

Wagner et al., in EP 0 503 162 (published Sep. 16, 1992) disclose azole derivatives of the general Formula (A) and the specific compound Example 150.

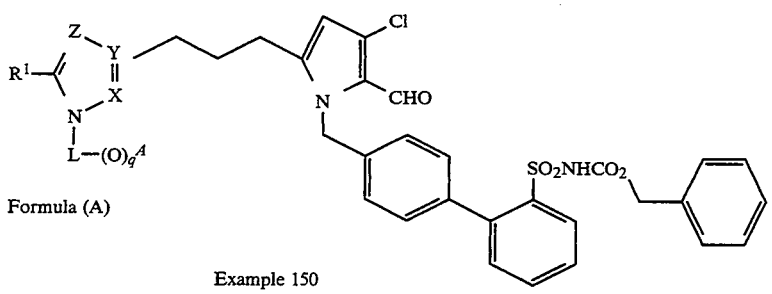

Formula (A)

Example 150

These compounds are disclosed to be antagonists of AII which are useful for treating cardiovascular disorders such as hypertension.

P. Herold and P. Bühlmayer in EP 0 407 342 A2 disclose substituted pyrimidinones, pyrimidinethiones, and pyrimidinimines of the formula:

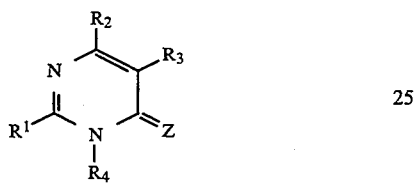

These are claimed to be antagonists of AII which are useful for treating hypertension.

E. Allen, et al. in EP 0 419 048 A (filed Aug. 21, 1990) disclose a similar series of pyrimidinones which are claimed to be antagonists of AII useful for the treatment of CHF and elevated intraocular pressure.

SUMMARY OF THE INVENTION

The present invention provides novel angiotensin II receptor antagonists of formula (I), pharmaceutical compositions containing compounds of formula (I) and therapeutic methods using them

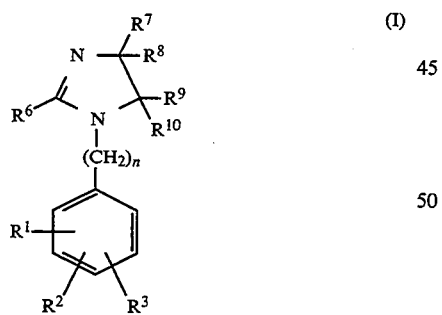

wherein:

$R^1$ is other than in the ortho position and is:

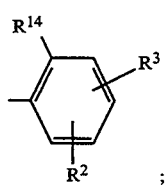

$R^2$ is
(a) H (b) halo (F, Cl, Br, I),
(c) $C_1$-$C_4$ alkyl,
(d) $C_1$-$C_4$ alkoxy,
(e) $C_1$-$C_4$ acyloxy,
(f) $C_1$-$C_4$ alkylthio,
(g) $C_1$-$C_4$ alkylsulfinyl,
(h) $C_1$-$C_4$ alkylsulfonyl,
(i) hydroxy ($C_1$-$C_4$) alkyl,
(j) aryl ($C_1$-$C_4$) alkyl,
(k) —$CO_2H$,
(l) —CN,
(m) tetrazol-5-yl,
(n) —$CONHOR^{13}$,
(o) —$SO_2NHR^{23}$,
(p) —$NH_2$,
(q) $C_1$-$C_4$ alkylamino,
(r) $C_1$-$C_4$ dialkylamino,
(s) —$NHSO_2R^{24}$,
(t) —$NO_2$,
(u) furyl,
(v) aryl,
wherein aryl is phenyl optionally substituted with one or two substituents selected from the group consisting of halo, $C_1$-$C_4$ alkyl, $C_1$-$C_4$ alkoxy, —$NO_2$, —$CF_3$, $C_1$-$C_4$ alkylthio, —OH, —$NH_2$, $C_1$-$C_4$ alkylamino, $C_1$-$C_4$ dialkylamino, —CN, —$CO_2H$, —$CO_2CH_3$, —$CO_2CH_2CH_3$, —$CO_2$benzyl;

$R^3$ is
(a) H,
(b) halo,
(c) $C_1$-$C_4$ alkyl,
(d) $C_1$-$C_4$ alkoxy,
(e) $C_1$-$C_4$ alkoxyalkyl;

$R^4$ is
(a) —CN,
(b) —$NO_2$,
(c) —$CO_2R^{11}$;

$R^5$ is
(a) H,
(b) $C_1$-$C_6$ alkyl,
(c) $C_3$-$C_6$ cycloalkyl,
(d) $C_2$-$C_4$ alkenyl,
(e) $C_2$-$C_4$ alkynyl;

$R^6$ is
(a) $C_1$-$C_{10}$ alkyl,
(b) $C_3$-$C_8$ alkenyl,
(c) $C_3$-$C_8$ alkynyl,
(d) $C_3$-$C_8$ cycloaklyl
(e) $C_4$-$C_8$ cycloalkenyl,
(f) $C_4$-$C_{10}$ cycloalkylalkyl,
(g) $C_5$-$C_{10}$ cycloalkylalkenyl,
(h) $C_5$-$C_{10}$ cycloalkylalkynyl,
(i) —$(CH_2)_sZ^2(CH_2)_mR^5$, (j) phenyl, optionally substituted with 1-2 substituents selected from the group of halo, $C_1$-$C_4$ alkyl, $C_1$-$C_4$ alkoxy, nitro, amino, hydroxy and benzyloxy;

(k) benzyl, optionally substituted on the phenyl ring with 1-2 substituents selected from the group of halo, $C_1$-$C_4$ alkyl, $C_1$-$C_4$ alkoxy or —$NO_2$;

$R^7$, $R^8$, $R^9$, and $R^{10}$ are independently chosen from
  (a) H,
  (b) $C_1$-$C_8$ alkyl unsubstituted or substituted by one or more halogen,
  (c) $C_3$-$C_6$ cycloalkyl,
  (d) $NO_2$,
  (e) CN,
  (f) $CONR^{15}R^{16}$
  (g) $CO_2R^{17}$,
  (h) $OR^{18}$,
  (i) $(CH_2)_nCONR^{15}R^{16}$ where n is 1–4,
  (j) $(CH_2)_nCO_2R^{17}$ where n is 1–4,
  (k) $(CH_2)_nOR^{18}$ where n is 1–4,
  (l) aryl, wherein aryl is as defined above,
  (m) $CH_2$aryl, wherein aryl is as defined above;

$R^7$ and $R^8$ taken together can be S, O, $NR^{19}$ or $CR^{11}R^{12}$;

$R^9$ and $R^{10}$ taken together can be —$(CH_2)_r$—, —$(CH_2)_nX(CH_2)_m$—, or $NR^{19}$;

$R^9$ and $R^{10}$ taken together can be S or O provided that $R^7$ and $R^8$ independently or when taken together are not $C_1$-$C_8$ alkyl unsubstituted or $C_1$-$C_8$ alkyl substituted with a substituent selected from the group of halogen, $C_3$-$C_6$ cycloalkyl, $(CH_2)_nOR^{18}$, aryl, wherein aryl is defined as above or —$(CH_2)_r$—;

$R^7$ and $R^9$ can be taken together to form an imide —$CONR^{22}CO$—;

$R^7$ and $R^9$ taken together can be —$CH_2NR^{22}CH_2$—, provided that both $R^7$, $R^8$ and $R^9$, $R^{10}$ are not S, O, $NR^{19}$ or —$(CH)_r$—;
  (n) (3-indolyl)methyl,
  (o) (4-imidazolyl)methyl;

$R^{11}$ and $R^{12}$ are independently
  (a) H,
  (b) $C_1$-$C_6$ alkyl,
  (c) $C_3$-$C_6$ cycloalkyl,
  (d) phenyl,
  (e) benzyl,
  (f) $R^{11}$ and $R^{12}$ when taken together can be —$CH_nXCH_n$—;

$R^{13}$ is
  (a) H,
  (b) methyl,
  (c) benzyl;

$R^{14}$ is
  (a) —$CO_2H$,
  (b) —$CH_2CO_2H$,
  (c) —$C(CF_3)_2OH$,
  (d) —$CONHNHSO_2CF_3$,
  (e) —$CONHOR^{13}$,
  (f) —$CONHSO_2R^{24}$,
  (g) —$CONHSO_2NHR^{23}$,
  (h) —$C(OH)R^{23}PO_3H_2$,
  (i) —$NHCOCF_3$,
  (j) —$NHCONHSO_2R^{24}$,
  (k) —$NHPO_3H_2$,
  (l) —$NHSO_2R^{24}$,
  (m) —$NHSO_2NHCOR^{24}$,
  (n) —$OPO_3H_2$,
  (o) —$OSO_3H$,
  (p) —$PO(OH)R^{23}$,
  (q) —$PO_3H_2$,
  (r) —$SO_3H$,
  (s) —$SO_2NHR^{23}$,
  (t) —$SO_2NHCOR^{24}$,
  (u) —$SO_2NHCONHR^{23}$,

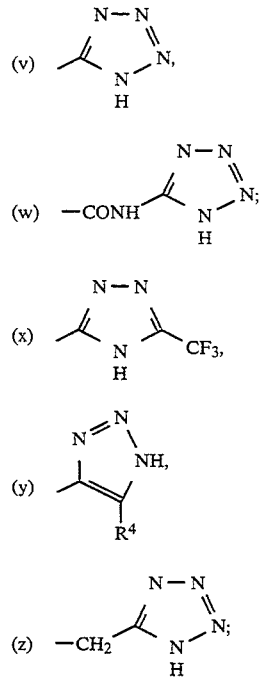

$R^{15}$ and $R^{16}$ are independently
  (a) H,
  (b) $C_1$-$C_6$ alkyl,
  (c) aryl, wherein aryl is as defined above,
  (d) aryl ($C_1$-$C_4$) alkyl, wherein aryl is as defined above;

$R^{15}$ and $R^{16}$ when taken together can constitute a
  (a) piperidine ring,
  (b) morpholine ring,
  (c) piperazine ring, optionally N-substituted with $C_1$-$C_6$ alkyl, phenyl or benzyl;

$R^{17}$ is
  (a) H,
  (b) $C_1$-$C_6$ alkyl,
  (c) phenyl,
  (d) benzyl;

$R^{18}$ is
  (a) H,
  (b) $C_1$-$C_6$ alkyl,
  (c) phenyl,
  (d) benzyl;

$R^{19}$ is
  (a) H,
  (b) $OR^{18}$
  (c) $C_1$-$C_6$ alkyl,
  (d) aryl,
  (e) $C_1$-$C_6$ alkyl aryl, wherein aryl is as defined above,
  (f) $NR^{20}R^{21}$;

$R^{20}$ and $R^{21}$ are independently
  (a) H,
  (b) $C_1$-$C_6$ alkyl,
  (c) phenyl, (d) benzyl, $R^{20}$ and $R^{21}$ taken togther can constitute a
(a) piperidine ring,
(b) morpholine ring,
(c) piperazine ring, optionally N-substituted with $C_1$-$C_6$ alkyl, phenyl or benzyl;

$R^{22}$ is
(a) H,
(b) $C_1$-$C_6$ alkyl,
(c) benzyl;

$R^{23}$ is
(a) H,
(b) $C_1$-$C_5$ alkyl,
(c) aryl,
(d) —$CH_2$—aryl, where aryl is defined as above,
(e) heteroaryl;
wherein heteroaryl is an unsubstituted, monosubstituted or disubstituted 5- or 6-membered aromatic ring which can optionally contain from 1 to 3 heteroatoms selected from the group consisting of O, N, and S and wherein the substituents are members selected from the group consisting of —OH, —SH, $C_1$-$C_4$ alkyl, $C_1$-$C_4$ alkoxy, —$CF_3$, halo, —$NO_2$, —$CO_2H$, —$CO_2CH_3$, —$CO_2$-benzyl, —$NH_2$, $C_1$-$C_4$ alkylamino, or $C_1$-$C_4$ dialkylamino;

$R^{24}$ is
(a) aryl, where aryl is as defined above,
(b) $C_3$-$C_7$ cycloalkyl,
(c) $C_1$-$C_4$ perfluoroalkyl,
(d) $C_1$-$C_4$ alkyl optionally substituted with a substituent selected from the group consisting of aryl as defined above, heteroaryl as defined above, —OH, —SH, $C_1$-$C_4$ alkyl, $C_1$-$C_4$ alkoxy, $C_1$-$C_4$ alkylthio, —$CF_3$, halo, —$NO_2$, —$CO_2H$, —$CO_2CH_3$, —$CO_2$-benzyl, —$NH_2$, $C_1$-$C_4$ alkylamino, $C_1$-$C_4$ dialkylamino, or —$PO_3H_2$,
(e) $C_1$-$C_4$ alkoxy optionally substituted with a substituent selected from the group consisting of aryl as defined above, heteroaryl as defined above, —OH, —SH, $C_1$-$C_4$ alkyl, $C_1$-$C_4$ alkoxy, $C_1$-$C_4$ alkylthio, —$CF_3$, halo, —$NO_2$, —$CO_2H$, —$CO_2CH_3$, —$CO_2$-benzyl, —$NH_2$, $C_1$-$C_4$ alkylamino, $C_1$-$C_4$ dialkylamino, —$PO_3H_2$, or
(f) heteroaryl where heteroacryl is as defined above;

X is
(a) S,
(b) O,
(c) —$NR^{22}$—;

Z is
(a) —O—,
(b) —S—,
(c) —$NR^{11}$—;

m is 1 to 5;
n is 1 to 4;
s is 0 to 5;
t is 2 to 5;
or a pharmaceutically acceptable salt thereof.

Preferred compounds of this invention are those of formula (I) wherein
$R^1$ is in the para position and is

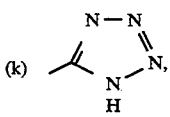

$R^6$ is
(a) $C_1$-$C_{10}$ alkyl, unsubstituted or substituted with one or more halogen
(b) $C_3$-$C_{10}$ alkenyl,
(c) $C_3$-$C_{10}$ alkynyl,
(d) $C_3$-$C_8$ cycloalkyl,
(e) phenyl, optionally substituted with 1-2 substituents selected from the group of halo, $C_1$-$C_4$ alkyl, $C_1$-$C_4$ alkoxy, nitro, amino, hydroxy and benzyloxy;
(f) benzyl, optionally substituted on the phenyl ring with one or two substitutents selected from the group consisting of halo, $C_1$-$C_4$ alkyl, $C_1$-$C_4$ alkoxy and —$NO_2$;

$R^7$, $R^8$, $R^9$, $R^{10}$ are independently
(a) H,
(b) $C_1$-$C_8$ alkyl unsubstituted or substituted by one or more halogen,
(c) $C_3$-$C_6$ cycloalkyl
(d) aryl, wherein aryl is as defined above;

$R^7$ and $R^8$ taken together can be S, O, $NR^{19}$ or $CR^{11}R^{12}$;

$R^9$ and $R^{10}$ taken together can be —$(CH_2)_r$—, —$(CH_2)_nX(CH_2)_m$ or $NR^{19}$, provided that $R^9$ and $R^{10}$ are not taken together to form $NR^{19}$ or —$(CH_2)_t$—, when $R^7$ and $R^8$ are taken together to form S, O, $NR^{19}$;

$R^9$ and $R^{10}$ taken together can be S or O provided that $R^7$ and $R^8$ independently or when taken together are not $C_1$-$C_8$ alkyl unsubstituted or $C_1$-$C_8$ alkyl substituted with a substituent selected from the group of halogen, $C_3$-$C_6$ cycloalkyl, $(CH_2)_nOR^{18}$, aryl, wherein aryl is defined as above or —$(CH_2)_r$—;

$R^{14}$ is
(a) —$CO_2H$,
(b) —$CONHSO_2R^{24}$,
(c) —$NHCONHSO_2R^{24}$,
(d) —$NHSO_2R^{24}$,
(e) —$NHSO_2NHCOR^{24}$,
(f) —$PO_3H_2$,
(g) —$SO_3H$,
(h) —$SO_2NHR^{23}$,
(i) —$SO_2NHCOR^{24}$,
(j) —$SO_2NHCONHR^{23}$, (k) 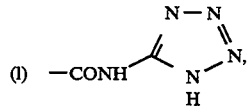

(l) —CONH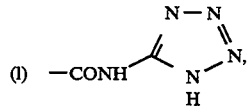

or a pharmaceutically acceptable salt thereof.

Still more preferred are compounds of the above preferred scope formula (I) wherein $R^2$ is
(a) H
(b) halo,
(c) $C_1-C_4$ alkyl,
(d) $C_1-C_4$ alkoxy;

$R^6$ is
(a) $C_1-C_7$ alkyl,
(b) $C_3-C_4$ alkenyl,
(c) $C_1-C_4$ alkynyl;
(d) phenyl, optionally substituted with 1–2 substituents selected from the group of halo, $C_1-C_4$ alkyl, $C_1-C_4$ alkoxy, nitro, amino, hydroxy and benzyloxy;

$R^{14}$ is
(a) —$CO_2H$,
(b) —$CONHSO_2R^{24}$,
(c) —$NHCONHSO_2R^{24}$,
(d) —$NHSO_2R^{24}$,
(e) —$NHSO_2NHCOR^{24}$,
(f) —$SO_2NHR^{23}$,
(g) —$SO_2NHCOR^{24}$,
(h) —$SO_2NHCONHR^{23}$, (i) 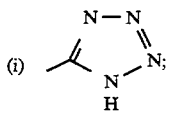

or a pharmaceutically acceptable salt thereof.

Most preferred due to their activity as angiotensin II antagonists are compounds of the more preferred scope wherein $R^1$ is

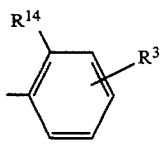

or a pharmaceutically acceptable salt thereof.

Illustrative of the most preferred compounds of the invention are the following:

1,5-dihydro-5,5-dimethyl-2-propyl-1-[(2'-(1H-tetrazol-5-yl)(1,1'-biphenyl)-4-yl)methyl]-4H-imidazol-4-one 1,5-dihydro-5,5-dimethyl-2-butyl-1-[(2'-(1H-tetrazol-5-yl)(1,1'-biphenyl)-4-yl)methyl]-4H-imidazol-4-one 1,5-dihydro-5,5-dimethyl-2-butenyl-1-[(2'-(1H-tetrazol-5-yl)(1,1'-biphenyl)-4-yl)methyl]-4H-imidazol-4-one 1,5-dihydro-5,5-ditrifluoromethyl-2-propyl-1-[(2'-(1H-tetrazol-5-yl)(1,1'-biphenyl)-4-yl)methyl]-4H-imidazol-4-one 1,5-dihydro-5,5-dicyclopropyl-2-propyl-1-[(2'-(1H-tetrazol-5-yl)(1,1'-biphenyl)-4-yl)methyl]-4H-imidazol-4-one 1,5-dihydro-5,5-dimethyl-2-butenyl-1-[(2'-(N-((phenylsulfonyl)carboxamido)biphen-4-yl)methyl]-4H-imidazol-4-one 1,5-dihydro-5,5-dimethyl-2-propyl-1-[(2'-(trifluoromethanesulfonylamido)biphen-4-yl)methyl]-4H-imidazol-4-one 1,5-dihydro-5,5-dimethyl-2-propyl-1-[(2'-(N-benzoylsulfonamido)biphen-4-yl)methyl]-4H-imidazol-4-one 1,5-dihydro-5,5-dimethyl-2-propyl-1-[(2'-(N-(4-chloro)-benzoylsulfonamido)biphen-4-yl)methyl]-4H-imidazol-4-one 1,5-diazaspiro-((4.5))-deca-3-ene-2-propyl-1-[(2'-(1H-tetrazol-5-yl)-(1,1'-biphenyl)-4-yl)methyl]-4H-imidazol-4-one 3,5-dihydro-5-(1-phenylethylidene)-2-propyl-3-[(2'(1H-tetrazol5yl)(1,1'-biphenyl)4yl)methyl]-4H-imidazol-4-one 1,5-dihydro-5,5-dimethyl-2-propyl-1-[(2'-(N-hexanoylsulfonamido)biphen-4-yl)methyl]-4H-imidazol-4-one 1,5-dihydro-5,5-dimethyl-2-propyl-1-[(2'-(N-trifluoroacetylsulfonamido)biphen4yl)methyl]-4H-imidazol-4-one 4'-(1,5-dihydro-5,5-dimethyl-2-propyl-4H-imidazol-4-one-1-yl-methyl)3'-methyl(1,1'-biphenyl-2-yl)sulfonyl carbamic acid n-butyl ester 4'-(3,5-dihydro-5(1-phenylethylidene)-2-propyl-4H-imidazol-4-one-3yl-methyl)-3'-methyl(1,1'-biphenyl-2-yl)sulfonyl carbamic acid n-butyl ester 4'-(1,5-dihydro-5,5-dimethyl-2-propyl-4H-imidazol-4-one-1-yl-methyl)-3'-methyl(1,1'-biphenyl-2-yl)sulfonyl carbamic acid (2-methylpropyl)ester 4'-(1,5-dihydro-5,5-dimethyl-2-butyl-4H-imidazol-4-one-1-yl-methyl)-3'-methyl(1,1'-biphenyl-2-yl)sulfonyl carbamic acid n-butyl ester 4'-(1,5-dihydro-5,5-dimethyl-2-butyl-4H-imidazol-4-one-1-yl-methyl)-3'-methyl(1,1'biphenyl-2-yl)sulfonyl carbamic acid (2-methylpropyl)ester 4'-(1,5-dihydro-5,5-ditrifluoromethyl-2-propyl-1-4H-imidazol-4-one-1-yl-methyl)-3'-methyl(1,1'-biphenyl-2-yl)sulfonyl carbamic acid (2-methylpropyl)ester 4'-(1,5-dihydro-5,5-dicyclopropyl-2-propyl-1-4H-imidazol-4-one-1-yl-methyl)-3'-methyl(1,1'-biphenyl-2-yl)sulfonyl carbamic acid n-butyl ester.

Pharmaceutically suitable salts include both the metallic (inorganic) salts and organic salts; a list of which is given in Remington's Pharmaceutical Sciences, 17th Edition, p. 1418 (1985). It is well known to one skilled in the art that an appropriate salt form is chosen based on physical and chemical stability, flowability, hydroscopicity, and solubility. Preferred salts of this invention for reasons cited above include potassium, sodium, calcium, and ammonium salts.

DETAILED DESCRIPTION

Synthesis

The compounds of formula (I) may be prepared using the reactions and techniques described in this section. The reactions are performed in solvent suitable to the reagents and materials employed and suitable for the transformation being effected. It is understood by those skilled in the art of organic synthesis that the functionality present on the imidazole and other portions of the molecule must be consistent with the chemical transformations proposed. This will frequently necessitate judgment as to the order of synthetic steps, protecting groups required, deprotection conditions and activation of a benzylic position to enable attachment to nitrogen on the imidazole nucleus. Throughout the following section, not all compounds of formula (I) falling into a given class may necessarily be prepared by all the methods described for that class. Substituents on the starting materials may be incompatible with some of the reaction conditions required in some of the methods described. Such restrictions to the substituents which are compatible with the reaction conditions will be readily apparent to one skilled in the art and alternative methods described must then be used. The compounds of this application that have a chiral center may be resolved into the pure or partially pure optical isomers by any of the appropriate procedures known to those skilled in the art.

The compounds of the present invention can be prepared by reaction of a sulfonamide of Formula 2 with an acylating reagent such as an acyl halide or acyl imidazole, or an alkyl chroroformate, or a carbamoylating reagent such as an isocyanate, (Scheme 1). Alcohol exchange can also be performed on compounds of Formula 36 by heating with excess of the desired alcohol to give new compounds within the present invention. The sulfonamides (2) can be prepared as described in European Application EP479,479, which is hereby incorporated by reference, and as shown in Scheme 1a.

SCHEME 1

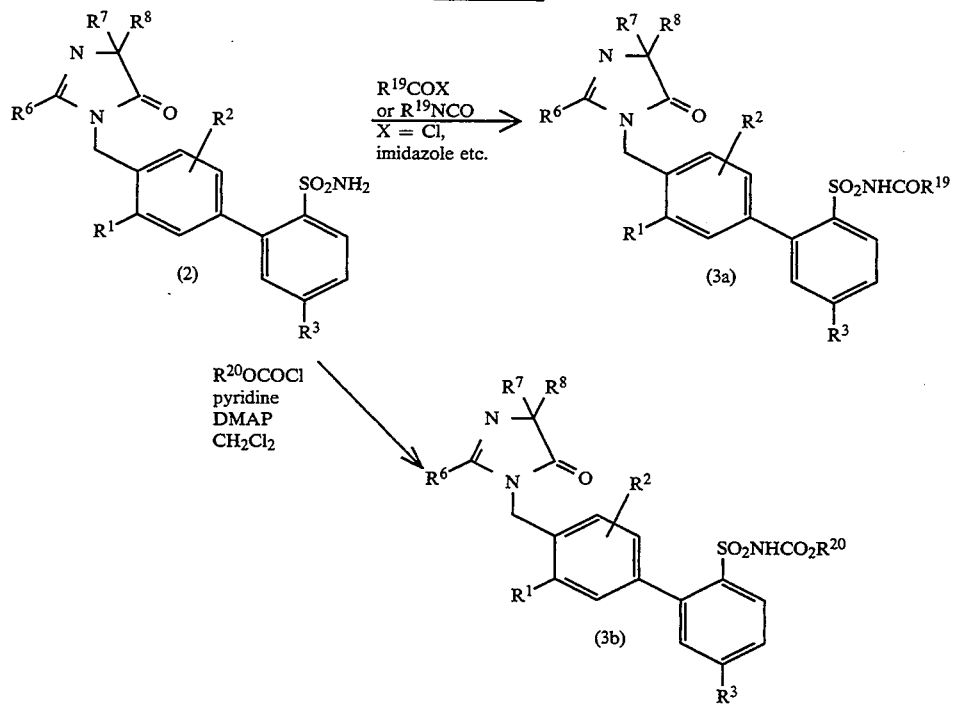

The alkylation produces a mixture of the two regioisomers using ether sodium hydride or potassium carbonate as base. The $N^1$ regioisomer is the major and the $N^3$ is the minor products. These two isomers can be separated and purified using conventional separation techniques such as chromatography or crystallization. In those cases where separation of regioisomers is difficult by conventional techniques, the mixture can be transformed into suitable derivatives that can be separated by usual separation methods. They possess distinct physical and biological properties.

SCHEME 1a

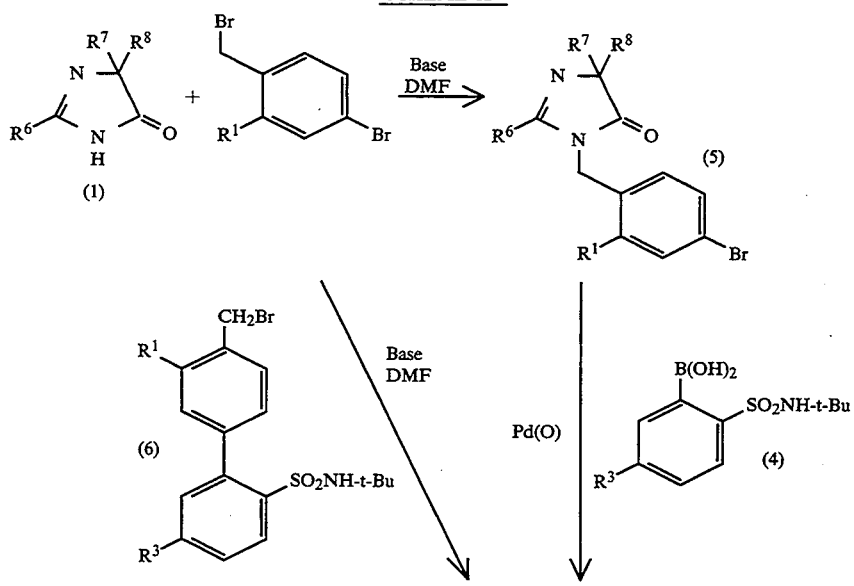

SCHEME 1a

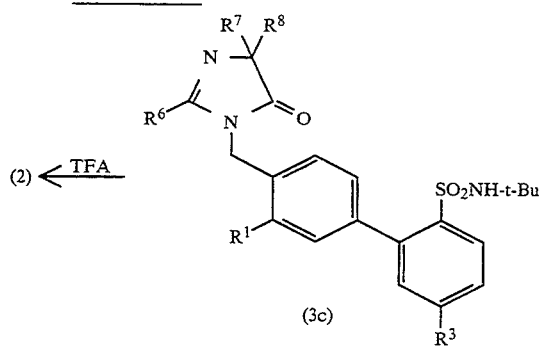

-continued

The biphenyl intermediates of formula 6 can be prepared as described in European Patent Applications EP479,479 and references therein, or as shown in Scheme 2. The boronic acid (4) may be prepared by lithiation of sulfonamide (4a) followed by treatment with triisopropyl borate and hydrolysis as shown in Scheme 2.

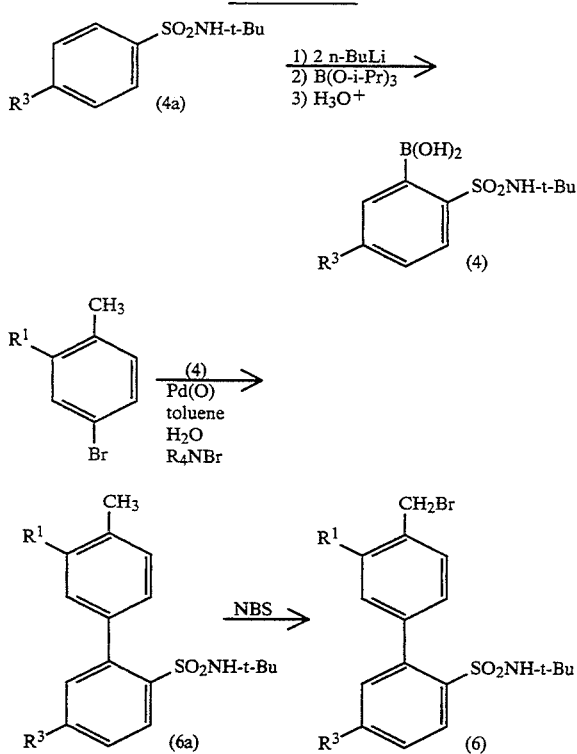

The starting imidazolinones are readily available by any number of standard methods. For example, imidazolinone of formula 1 can be prepared as shown in Scheme 3. The amino nitrile 7 is readily obtainable from aldehydes and ketones via the Strecker Synthesis and various modifications thereof ($R^7=R^8=CF_3$, Y. V. Zeifman, N. P. Gambaryan, I. L. Knunyants, Dokl. Acad. Nauk. S.S.S.R., 153, 1334, 1963). Treatment of the amino nitrile with triethyl amine and one equivalent of the appropriate acyl or aroyl chloride 8 in methylene chloride at room temperature overnight, gives the corresponding amidonitrile 9. Alternatively, the nitrile can be made following the procedure described in German patent disclosure DE3704100A1. The nitrile can be hydrolyzed to the diamide 10 using standard procedures such as treatment with hydrochloric acid followed by ammonium hydroxide. Treatment of the diamide with 1N sodium hydroxide as described in E. Mohr, J. Pract. Chem., 81, 49, 1910, gives the imidazolinone 1.

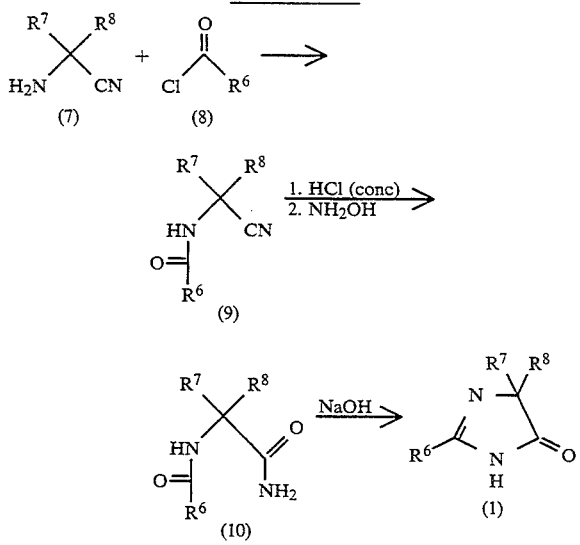

Alternatively, imidazolinones of formula 1 can also be prepared as shown in Scheme 4. Treatment of the amino acid 11 with tert-butyl pyrocarbonate 12 with two or more equivalents of base gives the BOC (tert-butyloxycarbonyl) protected amino acid 13, M. Bodanszky and A. Bodanszky, The Practice of Peptide Chemistry, 1984. The protected amino amide 14 can be synthesized from the active ester followed by ammonia. Deprotection using HCl gas gives the amino amide hydrochloride 15. Treatment with two or more equivalents of base and the appropriate acyl or aroyl chloride gives the diamide 10 which can be cyclized by treatment with 1N sodium hydroxide as described above.

SCHEME 4

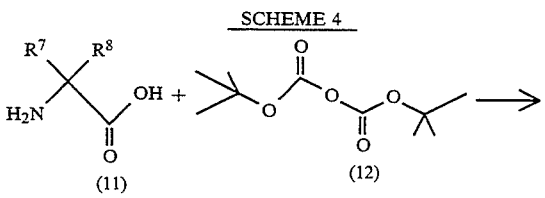

SCHEME 4 -continued

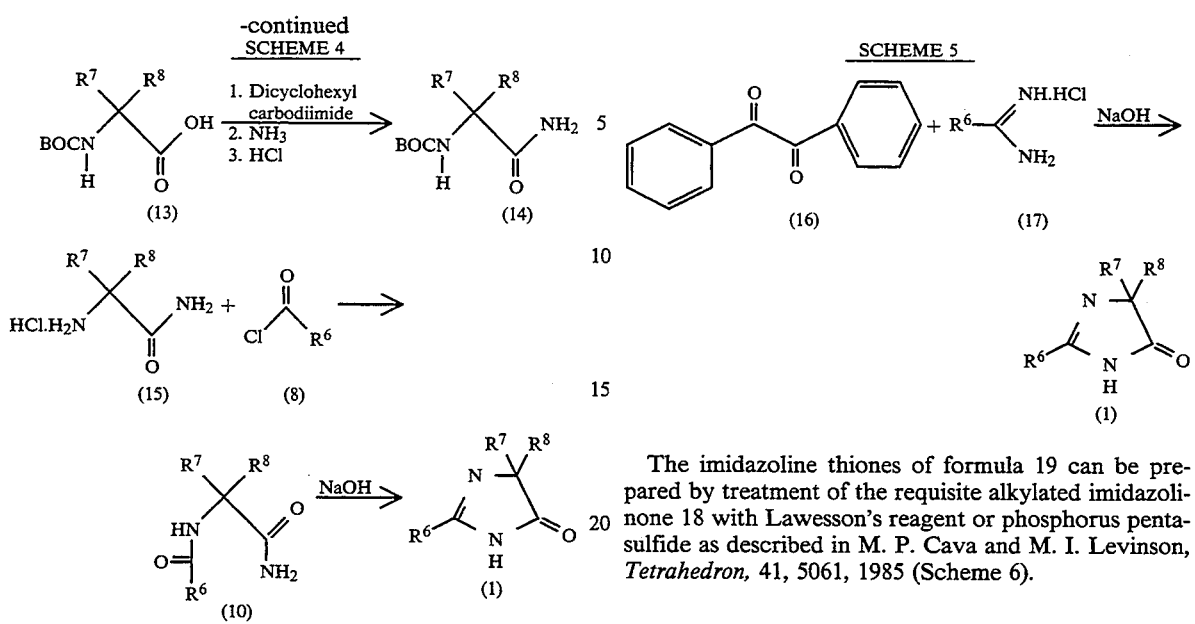

Likewise, compound 10 may be obtained by reacting amino acid with the requisite acid chloride by either a Schotten-Baumann procedure, or simply stirring in a solvent such as methylene chloride in the presence of base such as sodium bicarbonate, pyridine or triethyl amine followed by coupling reaction with ammonia via a variety of amide or peptide forming reactions such as DCC coupling, azide coupling, mixed anhydride synthesis or any other coupling procedure familiar to one skilled in the art.

The use of 1-amino-1-cycloalkylcarboxylic acids in the above procedure provides the imidazolinone starting materials for the preparation of the spiro-substituted imidazolinones of formula (1).

Imidazolinones of formula 1 can also be prepared following the procedure described in Japanese Patent disclosure JP 58055467.

Imidazolinones of formula 1 wherein $R^7$ and $R^8$ are both phenyl can be prepared as shown in Scheme 5 by reaction of benzil 16 with alkyl or aryl amidine hydrochloride 17, A. W. Cox, *Org. Syn.*, 1, 5, R. T. Boere, R. T. Oakley, R. W. Reed, *J. Organomet. Chem.*, 331, 161, 1987, in the presence of base such as 1N sodium hydroxide, G. Rio and A. Rajon, *Bull. Soc. Chim. France*, 543, 1958 and references therein.

The imidazoline thiones of formula 19 can be prepared by treatment of the requisite alkylated imidazolinone 18 with Lawesson's reagent or phosphorus pentasulfide as described in M. P. Cava and M. I. Levinson, *Tetrahedron*, 41, 5061, 1985 (Scheme 6).

SCHEME 6

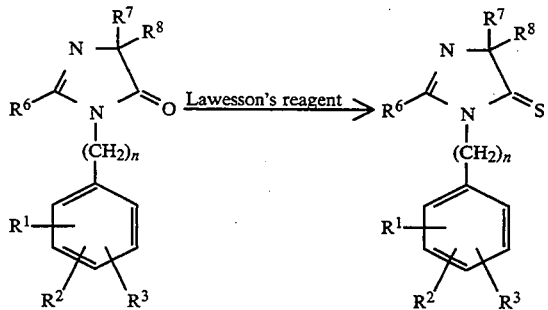

Compounds of formula 20 can be prepared by treatment of the requisite alkylated imidazolinone 18 with Meerwein's reagent, H. Meerwein, *Org. Syn.*, 5, 1080, 1973, in ether followed by treatment with ammonia, alkyl or aryl amines, hydroxyl amines or hydrazines, as shown in Scheme 7. The aminals of formula 21 can be prepared by reducing the requisite imines of formula 20 with lithium aluminum hydride in tetrahydrofuran or sodium borohydride in ethanol for 1 to 24 hours at room temperature to the boiling temperature of solvent. Alternatively, compounds of formula 20 can be prepared by alkylating the imines of formula 22 with the requisite benzyl halides 2.

SCHEME 7

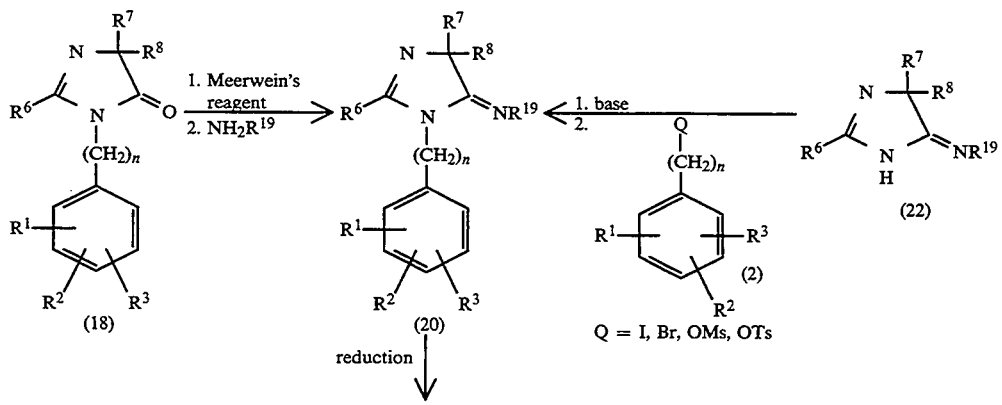

SCHEME 7 -continued

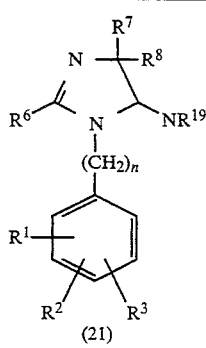

(21)

The imines of formula 22 can be prepared from base catalyzed cyclization reaction of the amido amidine 23 which was prepared by treatment of the amido nitrile of formula 9 with anhydrous HCl in ethanol followed by ammonia (Scheme 8).

SCHEME 8

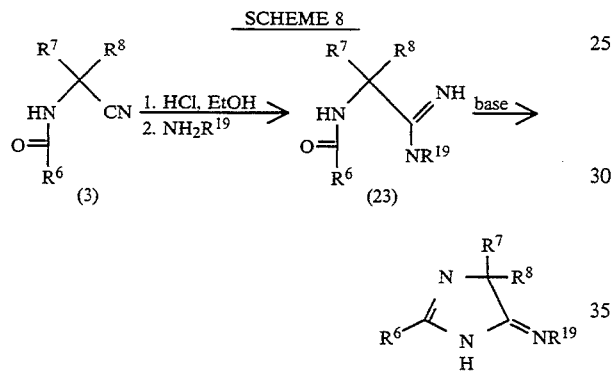

As shown in Scheme 9, the imidazoline thione of formula 24 wherein $R^7$ or $R^8$ cannot be hydrogen can be prepared by treating the requisite imidazolinone 1 with Lawesson's reagent or phosphorus pentasulfide as described in M. P. Cava and M. I. Levinson, *Tetrahedron*, 41, 5061, 1985. Alkylation using base such as sodium hydride followed by alkyl halide such as methyl iodide followed by oxidation with meta-chloroperbenzoic acid (MCPBA) gives the (methyl sulfonyl)imidazole 25 which can be subjected to nucleophilic displacement reaction with nucleophiles such as cyanide to give cyanoimidazoles 26. The cyanoimidazoles can be selectively reduced to give the cyanoimidazoline 27. The nitrile group can be further elaborated into other functional groups such as carboxylic acid 28, amidine 29, by methods familiar to one skilled in the art.

SCHEME 9

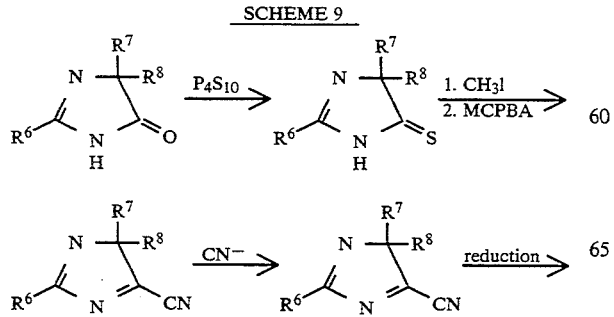

SCHEME 9 -continued

The cyanoimidazoline 30 can be hydrolyzed and cyclized using standard procedure such as treatment with hydrochloric acid and ethanol to form the cyclic imide (31, Scheme 10). Alkylation using base such as sodium hydride followed by alkyl halide gives the cyclic imide derivative 32 which can be reduced with reducing agent such as diisobutylaluminum hydride (DIBAL-H) or lithium aluminum hydride to give compound 33.

SCHEME 10

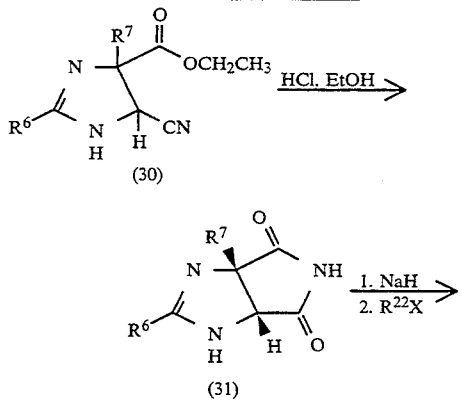

-continued
SCHEME 10

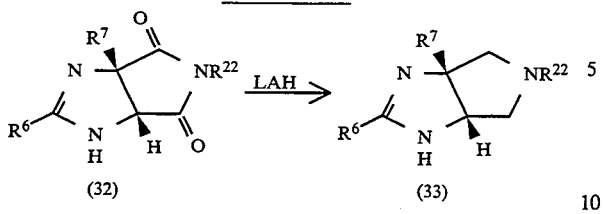

As shown in Scheme 11, the hydroxy imidazoline 34 can be prepared by reduction of the requisite imidazolinone wherein $R^7$ and/or $R^8$ cannot be hydrogen with reducing agents such as DIBAL-H. The hydroxyl group may be readily converted to the ethers 35 by a variety of procedures such as treatment with potassium t-butoxide, sodium hydride or the like in solvent such as dimethyl formamide followed by treatment with alkyl halide, tosylate or mesylate at room temperature for 1–24 hours. The hydroxyl group wherein $R^7$ and/or $R^8$ is not polyfluoro or perfluoroalkyl may be acylated to give esters of formula 38. Acylation can be achieved with 1–3 equivalents of an acyl halide or an anhydride in a solvent such as diethyl ether, methylene chloride in the presence of base such as triethyl amine or pyridine. The hydroxy imidazoline can be heated or treated with formic acid to form the acyliminium ion which can be treated with nucleophiles such as cyanide to form cyanoimidazoline 36 or amines to form aminoimidazoline 37.

base such as $K_2CO_3$ in organic solvent such as methylene chloride gives the free base.

SCHEME 12

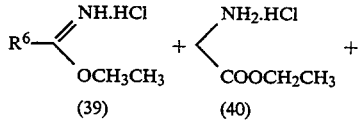

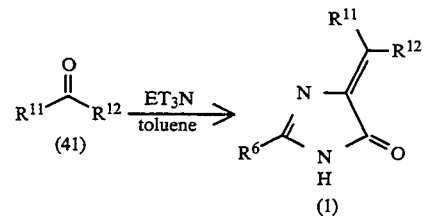

The compounds of this invention and their preparation can be understood further by the following examples which do not constitute a limitation of the invention. In these examples, unless otherwise indicated, all temperatures are in degrees centigrade and pans and percentages are by weight.

EXAMPLE 1

Preparation of 1,5-Dihydro-5,5-dimethyl-2-propyl-1-[(2'-(1H-tetrazol-5-yl)(1,1'-biphenyl)-4-yl)methyl]-4H-imidazol-4-one PART A: Preparation of 2-N-Butyramido-isobutyronitrile

SCHEME 11

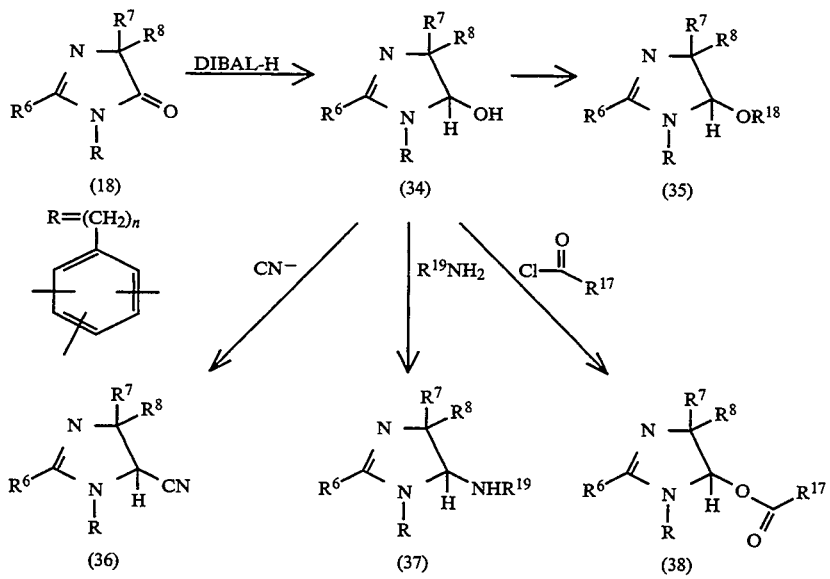

Imidazolinones of formula 1 wherein $R^7$ and $R^8$ taken together are $CR^{11}R^{12}$ can be prepared as described by J. Lamboy, J. Am. Chem. Soc., 76, 133, 1954, A. Jain and A. K. Mukerjee, J. Indian Chem. Soc., 65, 141, 1988, H. Lehr et al., J. Org. Chem., 75, 3640, 1953. Scheme 12 shows the reaction of alkyl or aryl imidate 39 with glycine ethyl ester hydrochloride 40 and a ketone 41 in refluxing toluene and tertiary base such as triethyl amine to give the desired imidazolinone. The imidate hydrochloride salt can be prepared by following McElvain, J. Am. Chem. Soc., 64, 1825, 1942. Treatment with trile Butyryl chloride (23.0 g, 0.22 mol) was added dropwise to a cooled mixture of 2-amino-isobutyronitrile (16.8 g, 0.20 mol) and triethyl amine (25 g, 0.25 mol) in methylene chloride (300 mL). The mixture was stirred for 3 hours at room temperature after which it was poured into 1N HCl (50 mL). The organic layer was washed with 1N HCl (2×50 mL), 1N NaOH (2×50 mL), dried (MgSO$_4$) and concentrated. The residue was triturated with hexane to give a pale yellow solid (18.2 g, 59%), m.p. 57.9–58.4; MS m/e 155.2 (M$^+$ +H) NMR (CDCl$_3$/TMS) d 0.96 (t, 3H, J=7 Hz, CH$_3$), 1.69 (m, 2H, CH$_2$), 1.70 (s, 6H, 2 CH$_3$), 2.18 (t, 2H, J=7 Hz, CH$_2$), 5.74 (s, 1H, NH).

PART B: Preparation of 2-N-Butyramido-isobutylamide

2-N-Butyramido isobutyronitrile (6.0 g, 38.9 mmol) was dissolved in concentrated hydrochloric acid (10 mL) at 0° C. Cold water (50 mL) was added immediately followed by treatment with concentrated ammonium hydroxide to pH 5–6. The mixture was extracted successively with methylene chloride. The organic layer was combined and concentrated to give white solid (5.4 g, 82%). M.P. 155.9–157.4, M.S. m/e 173.2 (M$^+$+H) NMR (CDCl$_3$/TMS) d 0.95 (t, 3H, J=7Hz, CH$_3$), 1.59 (s, 6H, 2 CH$_3$), 1.66 (m, 2H, CH$_2$), 2.17 (t, 2H, J=7 Hz, CH$_2$), 5.57 (s, 1H, NH), 6.10 (s, 1H, NH), 6.60 (s, 1H, NH).

PART C: Preparation of 2-Propyl-4,4-dimethyl-1H-imidazol-5(4H)-one

2-N-Butyramido-isobutylamide (5.4 g, 31.4 mmol) was dissolved in 1N sodium hydroxide (40 mL) and heated at 80° C. for 30 minutes. The mixture was cooled to room temperature and extracted successively with ethyl acetate. The combined organic layer was concentrated and the residue was chromatographed over silica gel eluting with ethyl acetate to give 2.1 g white solid: m.p. 66.5–68.5 M.S. m/e 155.2 (M$^+$+H) NMR (CDCl$_3$/TMS) d 1.01 (t, 3H, J=7 Hz, CH$_3$), 1.34 (s, 6H, 2 CH$_3$), 1.73 (m, 2H, CH$_2$), 2.44 (t, 2H, J=7 Hz, CH$_2$).

PART D: Preparation of 1,5-Dihydro-5,5-dimethyl-2-propyl-1-[(2'-(triphenyl methyl tetrazol-5-yl)(1,1'-biphenyl)-4-yl)methyl]-4H-imidazol-4-one A mixture of potassium carbonate (500 mg, 3.7 mmol), 2-propyl-4-4-dimethyl-1H-imidazol-5(4H)-one (0.6 g, 3.9 mmol), and 4'-bromomethyl-2-(triphenyl methyl tetrazol-5-yl)biphenyl (1.08 g, 1.9 mmol) in dimethyl formamide (5 mL) was allowed to stir at room temperature overnight. The mixture was chromatographed over silica gel eluting with ethyl acetate-hexane to give 1,5-dihydro-5,5-dimethyl-2-propyl-1-[(2'-(triphenyl methyl tetrazol-5-yl)(1,1'-biphenyl)-4-yl)methyl]-4H-imidazol-4-one (70 mg, 14% ) M.S. m/e 631.5 (M$^+$+H) NMR (CDCl$_3$/TMS) δ0.88 (t, 3H, J=7 Hz, CH$_3$), 1.38 (s, 6H, 2 CH$_3$), 1.67 (m, 2H, CH$_2$), 2.21 (t, 2H, J=7Hz, CH$_2$), 4.56 (s, 2H, CH$_2$), 6.92 (d, J=7 Hz, 8H, H$_{arom}$), 7.11 (d, J=7 Hz, 2H, H$_{arom}$), 7.24–7.38 (m, 10H, H$_{arom}$), 7.47 (m, 2H, H$_{arom}$), 7.92 (m, 1H, H$_{arom}$).

PART E: Preparation of 1,5-Dihydro-5,5-dimethyl-2-propyl-1-[(2'-(1H-tetrazol-5-yl)(1,1'-biphenyl)-4-yl)methyl]-4H-imidazol-4-one 1,5-Dihydro-5,5-dimethyl-2-propyl-1-[(2'-(triphenyl methyl tetrazol-5-yl)(1,1'-biphenyl)-4-yl)methyl]-4H-imidazol-4-one (60 mg, 0.1 mmol) in tetrahyrofuran (5 mL) and 10% hydrochloric acid (3 mL) was allowed to stir at room temperature overnight. The reaction mixture was treated with 50% sodium hydroxide to pH 8, concentrated and cooled in ice bath. The precipitate was filtered and the aqueous solution was adjusted to pH 3 using concentrated hydrochloric acid to give white solid which was recrystalized from ethyl acetate hexane to give amorphous solid (23 mg, 62%). M.P. 127.5–129.9 M.S. m/e 389.2 (M$^+$+H) NMR (CDCl$_3$/TMS) δ0.98 (t, 3H, J=7 Hz, CH$_3$), 1.50 (s, 6H, 2 CH$_3$), 1.76 (m, 2H, CH$_2$), 2.64 (t, 2H, J=7 Hz, CH$_2$), 4.77 (s, 2H, CH$_2$), 7.14 (s 4H, H$_{arom}$), 7.41–7.58 (m, 3H, H$_{arom}$), 7.90 (m, 1H, H$_{arom}$).

EXAMPLE 2

3,5-Dihydro-5-(1-phenylethylidene)-2-propyl-3-[(2'-(1H-tetrazol-5-yl)(1,1'-biphenyl)-4-yl)methyl]-4H-imidazol-4-one PART A: Preparation of 2-propyl-4-(1-phenylethyledene)-1H-imidazol-5(4H)-one To a mixture of acetophenone (1.2 mL, 0.01 mol), glycine ethyl ester hydrochloride (2.80 g, 0.02 mol) and ethyl butyrimidate (3.0 g, 0.02 mol) in 100 mL toluene was added triethyl amine (7.0 mL, 5 eq.). The mixture was heated at 80° C. under N$_2$ for 12 hours. The solvent was removed and the residue was partitioned between CH$_2$Cl$_2$ and water. The layers were separated. The aqueous layer was extracted with CH$_2$Cl$_2$. The combined organic layer was washed with brine, concentrated and chromatographed over silica gel eluting with 1:1 hexane:ethyl acetate, to give 0.35 g of the z isomer and 0.08 g of the E isomer. M.S. m/e 229 (M$^+$+H) Z isomer, NMR (CDCl$_3$/TMS) δ1.01 (t, 3H, CH$_3$), 1.76 (m, 2H, CH$_2$), 2.53 (t, 2H, CH$_2$), 2.73 (s, 3H, CH$_3$), 7.39 (m, 3H, H$_{arom}$), 7.78 (d, 2H, H$_{arom}$), 9.30 (S, 1H, NH). E isomer, NMR (CDCl$_3$/TMS) δ1.01 (t, 3H, CH$_3$), 1.72 (m, 2H, CH$_2$), 2.48 (t, 2H, CH$_2$), 2.50 (s, 3H, CH$_3$), 7.40 (m, 5H, H$_{arom}$), 9.00 (S, 1H, NH).

PART B: Preparation of 3,5-dihydro-5-(1-phenylethylidene)-2-propyl-3-[(2'-(triphenylmethyltetrazol-5-yl)(1,1'-biphenyl)-4-yl)methyl]-4H-imidazol-4-one Sodium hydride (0.15 g, 1.5 eq., 50% suspension in oil) was added to 0.2-propyl-4-(1-phenylethyledene)-1H-imidazol-5(4H)-one (0.47 g, 2.1 mmol) in dimethyl formamide (20 mL). The mixture was allowed to stir at room temperature for 15 minutes. 4'-Bromomethyl-2(triphenyl methyl tetrazol-5-yl) biphenyl (1.50 g, 1.28 eq.) was added and the reaction mixture was allowed to stir at room temperature overnight. The reaction mixture was poured into water and extracted with ether. The organic layer was washed successively with water and saturated sodium chloride solution, dried (MgSO$_4$) and concentrated. The residue was chromatographed over silica gel eluting with ethyl acetate-hexane 1:4 to give 3,5-dihydro-5-(1-phenylethyledene)-2-propyl-3-[(2'-(triphenyl methyl tetrazol-5-yl)(1,1'-biphenyl)-4-yl)methyl]-4H-imidazol-4-one (0.22 g, light yellow foam). NMR (CDCl$_3$/TMS) δ0.89 (t, 3H, CH$_3$), 1.60 (m, 2H, CH$_2$), 2.31 (m, 2H, CH$_2$), 2.80 (s, 3H, CH$_3$), 4.70 (s, 2H, CH$_2$), 6.91 (d, 6H, H$_{arom}$), 6.99 (d, 2H, H$_{arom}$), 7.10 (d, 2H, H$_{arom}$), 7.20–7.50 (m, 15H, H$_{arom}$), 7.80 (d, 2H, H$_{arom}$), 7.92 (d, 1H, H$_{arom}$).

PART C: Preparation of 3,5-dihydro-5-(1-phenylethylidene)-2-propyl-3-[(2'-(1H-tetrazol-5-yl)(1,1'-biphenyl)-4-yl)methyl]-4H-imidazol-4-one 3,5-dihydro-5-(1-phenylethylidene)-2-propyl-3-[(2'-(triphenylmethyltetrazol-5-yl)(1,1'-biphenyl)-4-yl)methyl]-4H-imidazol-4-one (0.17 g) in tetrahydrofuran (20 mL) and 10% hydrochloric acid (5 mL) was allowed to stir at room temperature for 3.5 hr. The reaction mixture was treated with 50% sodium hydroxide to pH 8, concentrated and cooled in ice bath. The precipitate was filtered and the aqueous solution was adjusted to pH 4–5 using concentrated hydrochloric acid to give white solid which was washed with cold water and dried to give yellow solid (80 mg) as a mixture of the Z and E isomers (8:2). M.S. m/e 463 (M$^+$+H) NMR (CDCl$_3$/TMS) δ0.98 (t, 3H, CH$_3$), 1.67 (m, 2H, CH$_2$), 2.39 (t, 2H, CH$_2$), 2.76 (s, 3H, CH$_3$), 4.80 (s, 2H, CH$_2$), 7.04–7.20 (m, 4H, H$_{arom}$), 7.42–7.61 (m, 2H, H$_{arom}$), 7.63 (d, 2H, H$_{arom}$), 7.99 (d, 1H, H$_{arom}$).

EXAMPLE 3

3,5-Dihydro-5-(diphenylmethylene)-2-propyl-3-[(2'-(1H-tetrazol-5-yl)(1,1'-biphenyl)-4-yl)methyl]-4H-imidazol-4-one A mixture of potassium carbonate (83 mg, 2 eq.), 2-propyl-4-(diphenylmethylene)-1H-imidazol-5(4H)-one (90 mg, 0.3 mmol), and 4'-bromomethyl-2-(triphenyl methyl tetrazol-5-yl)biphenyl (0.21 g, 1.2 eq.) in dimethyl formamide (10 mL) was allowed to stir at room temperature for 2 days. The solvent was in vacuo, the residue was dissolved in CH$_2$Cl$_2$ and washed with water and brine. The organic layer was dried over MgSO$_4$ and concentrated. The crude mixture was chromatographed over silica gel eluting with ethyl acetate-hexane (1:4) to give 3,5-dihydro-5-(diphenylmethylene)-2-propyl-3-[(2'-(triphenyl methyl tetrazol-5-yl)(1,1'-biphenyl)-4-yl)methyl]-4H-imidazol-4-one (100 mg). M.S. m/e 767 (M$^+$+H) NMR (CDCl$_3$/TMS) δ0.90 (m, 3H, CH$_3$), 1.65 (m, 2H, CH$_2$), 2.38 (m, 2H, CH$_2$), 4.62 (s, 2H, CH$_2$), 6.88–7.50 (m, 30H, H$_{arom}$), 7.61 (m, 2H, H$_{arom}$), 7.90 (d, 1H, H$_{arom}$). The above compound was detritylated following the procedure described in Example 2C, to give 61 mg of the desired product. M.S. m/e 524 (M$^+$+H) NMR (CDCl$_3$/TMS) d 1.01 (t, 3H, CH$_3$), 1.78 (m, 2H, CH$_2$), 2.49 (t, 2H, CH$_2$), 4.75 (s, 2H, CH$_2$), 7.12–7.41 (m, 15H, H$_{arom}$), 7.58 (m,2H, H$_{arom}$), 8.10 (d, 1H, H$_{arom}$).

Compounds 1–325 in Table 1 can be prepared by the procedures described in Examples 1, 2, 3 employing the appropriately substituted imidazolinones and benzyl halides.

TABLE 1

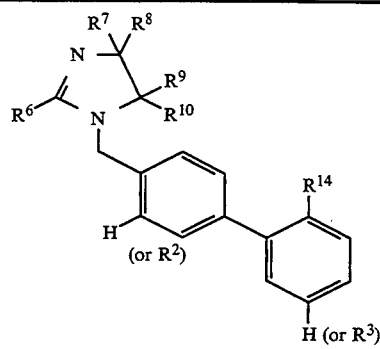

| Ex. | R$^6$ | R$^7$ | R$^8$ | R$^9$ | R$^{10}$ | R$^{14}$ | M.S. (M$^+$ + H) |
|---|---|---|---|---|---|---|---|
| 1 | n-Pr | | O | CH$_3$ | CH$_3$ | 1H-Tetrazol-5-yl | 389 |
| 2 | n-Pr | C(C$_6$H$_5$) | (CH$_3$) | | O | 1H-Tetrazol-5-yl | 463 |
| 3 | n-Pr | C(C$_6$H$_5$)$_2$ | | | O | 1H-Tetrazol-5-yl | 525 |
| 4 | n-Pr | | O | CH$_3$ | CH$_3$ | —CONHSO$_2$C$_6$H$_5$ | |
| 5 | n-Pr | | O | CH$_3$ | CH$_3$ | —SO$_2$NHCOC$_6$H$_5$ | |
| 6 | n-Pr | | O | CH$_3$ | CH$_3$ | —SO$_2$NHCO(n-C$_5$H$_{11}$) | |
| 7 | n-Pr | | O | CH$_3$ | CH$_3$ | —SO$_2$NHCO(cy-C$_3$H$_5$) | |
| 8 | n-Pr | | O | CH$_3$ | CH$_3$ | —SO$_2$NHCOCH$_2$C$_6$H$_5$ | |
| 9 | n-Pr | | O | CH$_3$ | CH$_3$ | —CO$_2$H | |
| 10 | n-Pr | | O | CH$_3$ | CH$_3$ | —CH$_2$CO$_2$H | |
| 11 | n-Pr | | O | CH$_3$ | CH$_3$ | —C(CF$_3$)$_2$OH | |
| 12 | n-Pr | | O | CH$_3$ | CH$_3$ | —CONHNSO$_2$CF$_3$ | |
| 13 | n-Pr | | O | CH$_3$ | CH$_3$ | —SO$_2$NHCOC$_6$H$_5$ (R$^2$ = CH$_3$) | |
| 14 | n-Pr | | O | CH$_3$ | CH$_3$ | —SO$_2$NHCO(n-C$_5$H$_{11}$) (R$^2$ = CH$_3$) | |
| 15 | n-Pr | | O | CH$_3$ | CH$_3$ | —SO$_2$NHCO(cy-C$_3$H$_5$) (R$^2$ = CH$_3$) | |
| 16 | n-Pr | | O | CH$_3$ | CH$_3$ | —CONHOCH$_3$(R$^2$ = CH$_3$) | |
| 17 | n-Pr | | O | CH$_3$ | CH$_3$ | —SO$_2$NHCO(n-Bu) (R$^2$ = CH$_3$) | |
| 18 | n-Pr | | O | CH$_3$ | CH$_3$ | —SO$_2$NHCOCH$_2$C$_6$H$_5$ (R$^2$ = CH$_3$) | |
| 19 | n-Pr | | O | CH$_3$ | CH$_3$ | —SO$_2$NHCONH(n-Bu) (R$^2$ = CH$_3$) | |
| 20 | n-Pr | | O | CH$_3$ | CH$_3$ | —NH—SO$_2$NHCO(n-Bu) (R$^2$ = CH$_3$) | |
| 21 | n-Pr | | O | CH$_3$ | CH$_3$ | —SO$_2$NHCO(i-C$_4$H$_9$) (R$^2$ = CH$_3$) | |
| 22 | n-Pr | | O | CH$_3$ | CH$_3$ | —CONHSO$_2$C$_2$H$_4$OH (R$^2$ = CH$_3$) | |
| 23 | n-Pr | | O | CH$_3$ | CH$_3$ | —CONHSO$_2$NH(4-ClC$_6$H$_4$) (R$^2$ = CH$_3$) | |
| 24 | n-Pr | | O | CH$_3$ | CH$_3$ | —C(OH)CH$_3$PO$_3$H$_2$ | |
| 25 | n-Pr | | O | CH$_3$ | CH$_3$ | —SO$_2$NHCOC$_6$H$_5$ (R$^2$ = Cl) | |
| 26 | n-Pr | | O | CH$_3$ | CH$_3$ | —SO$_2$NHCO(n-C$_5$H$_{11}$) (R$^2$ = Cl) | |
| 27 | n-Pr | | O | CH$_3$ | CH$_3$ | —SO$_2$NHCO(cy-C$_3$H$_5$) (R$^2$ = Cl) | |
| 28 | n-Pr | | O | CH$_3$ | CH$_3$ | —SO$_2$NHCO(i-C$_5$H$_{11}$) | |

TABLE 1-continued

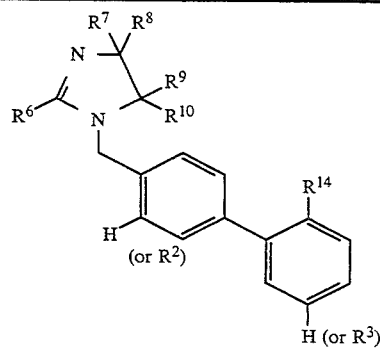

| Ex. | R⁶ | R⁷ | R⁸ | R⁹ | R¹⁰ | R¹⁴ | M.S. (M⁺ + H) |
|---|---|---|---|---|---|---|---|
| 29 | n-Pr | | O | CH₃ | CH₃ | —SO₂NHCO(n-Bu) (R² = Cl) | |
| 30 | n-Pr | | O | CH₃ | CH₃ | —SO₂NHCOCH₂C₆H₅ (R² = Cl) | |
| 31 | n-Pr | | O | CH₃ | CH₃ | —SO₂NHCONH(n-Bu) (R² = Cl) | |
| 32 | n-Pr | | O | CH₃ | CH₃ | NHCOCF₃ (R² = Cl) | |
| 33 | n-Pr | | O | CH₃ | CH₃ | —NHPO₂H (R² = Cl) | |
| 34 | n-Pr | | O | CH₃ | CH₃ | —NHCONH—SO₂(i-C₅H₁₁) (R² = Cl) | |
| 35 | n-Pr | | O | CH₃ | CH₃ | —NHSO₂(cy-C₃H₅) (R² = Cl) | |
| 36 | n-Pr | | O | CH₃ | CH₃ | —OPO₃H₂ (R² = Cl) | |
| 37 | n-Pr | | O | CH₃ | CH₃ | —SO₂NHCOC₆H₅ (R² = F) | |
| 38 | n-Pr | | O | CH₃ | CH₃ | —SO₂NHCO(n-C₅H₁₁) (R² = F) | |
| 39 | n-Pr | | O | CH₃ | CH₃ | —SO₂NHCO(cy-C₃H₅) (R² = F) | |
| 40 | n-Pr | | O | CH₃ | CH₃ | —SO₂NHCO(i-C₅H₁₁) (R² = F) | |
| 41 | n-Pr | | O | CH₃ | CH₃ | —SO₂NHCO(n-Bu) (R² = F) | |
| 42 | n-Pr | | O | CH₃ | CH₃ | —SO₂NHCOCH₂C₆H₅ (R² = F) | |
| 43 | n-Pr | | O | CH₃ | CH₃ | —SO₂NHCONH(n-Bu) (R² = F) | |
| 44 | n-Pr | | O | CH₃ | CH₃ | —OSO₃H (R² = F) | |
| 45 | n-Pr | | O | CH₃ | CH₃ | —PO(OH)(n-C₅H₁₁) (R² = F) | |
| 46 | n-Pr | | O | CH₃ | CH₃ | —PO₃H₂ (R² = F) | |
| 47 | n-Pr | | O | CH₃ | CH₃ | —SO₃H (R² = F) | |
| 48 | n-Pr | | O | CH₃ | CH₃ | —SO₂NH(4-C₅NH₄) (R² = F) | |
| 49 | n-Pr | | O | CH₃ | CH₃ | —SO₂NHCOC₆H₅ (R³ = n-Pr) | |
| 50 | n-Pr | | O | CH₃ | CH₃ | —SO₂NHCO(n-C₅H₁₁) (R³ = n-Pr) | |
| 51 | n-Pr | | O | CH₃ | CH₃ | —SO₂NHCO(cy-C₃H₅) (R³ = n-Pr) | |
| 52 | n-Pr | | O | CH₃ | CH₃ | —SO₂NHCO(i-C₅H₁₁) (R³ = n-Pr) | |
| 53 | n-Pr | | O | CH₃ | CH₃ | —SO₂NHCO(n-Bu) (R³ = n-Pr) | |
| 54 | n-Pr | | O | CH₃ | CH₃ | —SO₂NHCOCH₂C₆H₅ (R³ = n-Pr) | |
| 55 | n-Pr | | O | CH₃ | CH₃ | —SO₂NHCONH(n-Bu) (R³ = n-Pr) | |
| 56 | n-Pr | | O | CH₃ | CH₃ | —SO₂NH(n-Bu) (R³ = n-Pr) | |
| 57 | n-Pr | | O | CH₃ | CH₃ | —SO₂NHCONH(n-C₅H₁₁) (R³ = n-Pr) | |
| 58 | n-Pr | | O | CH₃ | CH₃ | —SO₂NHCONH(i-C₅H₁₁) (R³ = n-Pr) | |
| 59 | n-Pr | | O | CH₃ | CH₃ | —SO₂NHCONH(cy-C₃H₅) (R³ = n-Pr) | |
| 60 | n-Pr | | O | CH₃ | CH₃ | —SO₂NHCONHCH₂C₆H₅ (R³ = n-Pr) | |
| 61 | n-Pr | | O | CH₃ | CH₃ | —SO₂NHCOC₆H₅ (R² = Cl, R³ = n-Pr) | |
| 62 | n-Pr | | O | CH₃ | CH₃ | —SO₂NHCO(n-C₅H₁₁) (R² = Cl, R³ = n-Pr) | |
| 63 | n-Pr | | O | CH₃ | CH₃ | —SO₂NHCO(cy-C₃H₅) (R² = F, R³ = n-Pr) | |
| 64 | n-Pr | | O | CH₃ | CH₃ | —SO₂NHCO(i-C₅H₁₁) (R² = F, R³ = n-Pr) | |
| 65 | n-Pr | | O | CH₃ | CH₃ | —SO₂NHCO(n-Bu) (R² = Cl, R³ = n-Pr) | |
| 66 | n-Pr | | O | CH₃ | CH₃ | —SO₂NHCOCH₂C₆H₅ (R² = F, R³ = n-Pr) | |

TABLE 1-continued

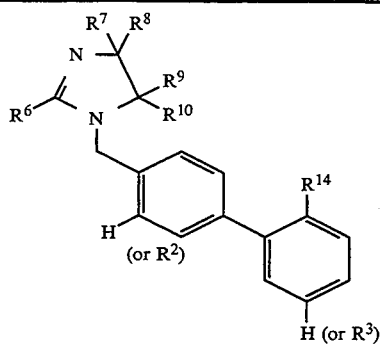

| Ex. | R6 | R7 | R8 | R9 | R10 | R14 | M.S. (M+ + H) |
|---|---|---|---|---|---|---|---|
| 67 | n-Pr | | O | CH3 | CH3 | —NHSO2NHCO(n-Bu) (R2 = Cl, R3 = n-Pr) | |
| 68 | n-Pr | | O | CH3 | CH3 | —NHSO2NHCO(n-C4H11) (R2 = F, R3 = n-Pr) | |
| 69 | n-Pr | | O | CH3 | CH3 | —NHSO2NHCO(i-C5H11) (R2 = Cl, R3 = n-Pr) | |
| 70 | n-Pr | | O | CH3 | CH3 | —NHSO2NHCO(cy-C3H5) (R2 = Cl, R3 = n-Pr) | |
| 71 | n-Pr | | O | CH3 | CH3 | —NHSO2NHCOCH2C6H5 (R2 = F, R3 = n-Pr) | |
| 72 | n-Pr | | O | CH3 | CH3 | —SO2NHCOCF3 | |
| 73 | n-Pr | | N | CH3 | CH3 | 1H-Tetrazol-5-yl | |
| 74 | n-Pr | | N | CH3 | CH3 | —SO2NHCO(4Cl-C6H4) | |
| 75 | n-Pr | | N | CH3 | CH3 | —SO2NHCO(n-C5H11) (R2 = CH3) | |
| 76 | n-Pr | | N | CH3 | CH3 | —NHSO2NHCO(n-C5H11) (R3 = n-Pr) | |
| 77 | n-Pr | | S | CH3 | CH3 | 1H-Tetrazol-5-yl | |
| 78 | n-Pr | | S | CH3 | CH3 | —SO2NHCO(4Cl-C6H4) | |
| 79 | n-Pr | | S | CH3 | CH3 | —SO2NHCO(n-C5H11) (R2 = CH3) | |
| 80 | n-Pr | | S | CH3 | CH3 | —NHSO2NHCO(n-C5H11) (R3 = n-Pr) | |
| 81 | n-Bu | | N | CH3 | CH3 | 1H-Tetrazol-5-yl | |
| 82 | n-Bu | | S | CH3 | CH3 | 1H-Tetrazol-5-yl | |
| 83 | n-Bu | | S | CH3 | CH3 | —NHSO2NHCO(n-Bu) | |
| 84 | n-Bu | | O | CH3 | CH3 | —CONHSO2C6H5 | |
| 85 | n-Bu | | O | CH3 | CH3 | —SO2NHCOC6H5 | |
| 86 | n-Bu | | O | CH3 | CH3 | —SO2NHCO(n-C5H11) | |
| 87 | n-Bu | | O | CH3 | CH3 | —SO2NHCO(cy-C3H5) | |
| 88 | n-Bu | | O | CH3 | CH3 | —SO2NHCOCH2Ph | |
| 89 | n-Bu | | O | CH3 | CH3 | —NHSO2NHCO(i-C4H9) | |
| 90 | n-Bu | | O | CH3 | CH3 | —NHSO2NHCO(n-Bu) | |
| 91 | n-Bu | | O | CH3 | CH3 | —NHSO2NHCO(n-C5H11) | |
| 92 | n-Bu | | O | CH3 | CH3 | —NHSO2NHCO(cy-C3H5) | |
| 93 | n-Bu | | O | CH3 | CH3 | —NHSO2NHCOCH2Ph | |
| 94 | n-Bu | | O | CH3 | CH3 | —SO2NHCO(4Cl—C6H4) | |
| 95 | n-Bu | | O | CH3 | CH3 | —SO2NHCO(n-C5H11) (R3 = n-Pr) | |
| 96 | n-Bu | | O | CH3 | CH3 | —SO2NHCO(n-C5H11) (R2 = CH3) | |
| 97 | n-Bu | | O | CH3 | CH3 | —NHSO2NHCO(n-C5H11) (R3 = n-Pr) | |
| 98 | n-Bu | | O | CH3 | CH3 | —NHSO2NHCO(n-Bu) (R2 = Cl) | |
| 99 | n-Bu | | O | CH3 | CH3 | —SO2NHCOCF3 | |
| 100 | n-Bu | | O | CH3 | CH3 | —SO2NHCO(n-C5H11) (R2 = Cl, R3 = n-Pr) | |
| 101 | n-Bu | | O | CH3 | CH3 | —NHSO2NHCO(i-C5H11) (R2 = F, R3 = n-Pr) | |
| 102 | n-Bu | | O | CH3 | CH3 | —SO2NHCONH(n-Bu) (R2 = Cl) | |
| 103 | n-Pr | | S | C2H5 | CH3 | —NHSO2NHCO(n-Bu) | |
| 104 | n-Pr | | O | C2H5 | CH3 | —CONHSO2C6H5 | |
| 105 | n-Pr | | O | C2H5 | CH3 | —SO2NHCOC6H5 | |
| 106 | n-Pr | | O | C2H5 | CH3 | —SO2NHCO(n-C5H11) | |
| 107 | n-Pr | | O | C2H5 | CH3 | —SO2NHCO(cy-C3H5) | |
| 108 | n-Pr | | O | C2H5 | CH3 | —SO2NHCOCH2Ph | |
| 109 | n-Pr | | O | C2H5 | CH3 | —NHSO2NHCO(i-C4H9) | |
| 110 | n-Pr | | O | C2H5 | CH3 | —NHSO2NHCO(n-Bu) | |
| 111 | n-Pr | | O | C2H5 | CH3 | —NHSO2NHCO(n-C5H11) | |
| 112 | n-Bu | | O | C2H5 | CH3 | —NHSO2NHCO(cy-C3H5) | |

TABLE 1-continued

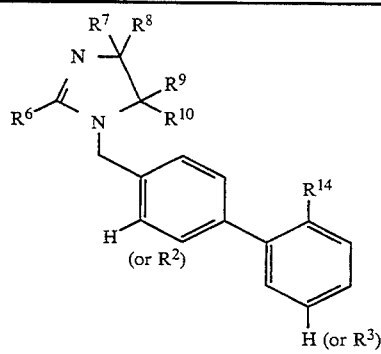

| Ex. | R6 | R7 | R8 | R9 | R10 | R14 | M.S. (M+ + H) |
|---|---|---|---|---|---|---|---|
| 113 | n-Bu | | O | C2H5 | CH3 | —NHSO2NHCOCH2Ph | |
| 114 | n-Bu | | O | C2H5 | CH3 | —SO2NHCO(4Cl—C6H4) | |
| 115 | n-Bu | | O | C2H5 | CH3 | —SO2NHCO(n-C5H11) (R3 = n-Pr) | |
| 116 | n-Bu | | O | C2H5 | CH3 | —SO2NHCO(n-C5H11) (R2 = CH3) | |
| 117 | n-Bu | | O | C2H5 | CH3 | —NHSO2NHCO(n-C5H11) (R3 = n-Pr) | |
| 118 | n-Bu | | O | C2H5 | CH3 | —NHSO2NHCO(n-Bu) (R2 = Cl) | |
| 119 | n-Bu | | O | C2H5 | CH3 | —SO2NHCOCF3 | |
| 120 | n-Bu | | O | C2H5 | CH3 | —SO2NHCO(n-C5H11) (R2 = Cl, R3 = n-Pr) | |
| 121 | n-Bu | | O | C2H5 | CH3 | —NHSO2NHCO(i-C5H11) (R2 = F, R3 = n-Pr) | |
| 122 | n-Bu | | O | C2H5 | CH3 | —SO2NHCONH(n-Bu) (R2 = Cl) | |
| 123 | n-Pr | | O | C2H5 | C2H5 | 1H-Tetrazol-5-yl | |
| 124 | n-Pr | | O | C2H5 | C2H5 | —CONHSO2C6H5 | |
| 125 | n-Pr | | O | C2H5 | C2H5 | —SO2NHCOC6H5 | |
| 126 | n-Pr | | O | C2H5 | C2H5 | —SO2NHCO(n-C5H11) | |
| 127 | n-Bu | | O | C2H5 | C2H5 | —SO2NHCO(cy-C3H5) | |
| 128 | n-Pr | | O | C2H5 | C2H5 | —SO2NHCOCH2Ph | |
| 129 | n-Bu | | O | CF3 | CF3 | —NHSO2NHCO(i-C4H9) | |
| 130 | n-Bu | | O | C2H5 | C2H5 | —NHSO2NHCO(n-Bu) | |
| 131 | n-Pr | | O | CF3 | CF3 | —NHSO2NHCO(n-C5H11) | |
| 132 | n-Pr | | O | CF3 | CF3 | —NHSO2NHCO(cy-C3H5) | |
| 133 | n-Bu | | O | CF3 | CF3 | —NHSO2NHCOCH2Ph | |
| 134 | n-Bu | | O | CF3 | CF3 | —SO2NHCO(4Cl—C6H4) | |
| 135 | pF—Ph | | O | CF3 | CF3 | —SO2NHCO(n-C5H11) (R3 = n-Pr) | |
| 136 | pF—Ph | | O | CH3 | CH3 | —SO2NHCO(n-C5H11) (R2 = CH3) | |
| 137 | pF—Ph | | O | CH3 | CH3 | —NHSO2NHCO(n-C5H11) (R3 = n-Pr) | |
| 138 | Ph | | O | CH3 | CH3 | —NHSO2NHCO(n-Bu) (R2 = Cl) | |
| 139 | Ph | | O | CH3 | CH3 | —SO2NHCOCF3 | |
| 140 | Ph | | O | CH3 | CH3 | —SO2NHCO(n-C5H11) (R2 = Cl, R3 = n-Pr) | |
| 141 | CH3 | | O | CH3 | CH3 | —NHSO2NHCO(i-C5H11) (R2 = F, R3 = n-Pr) | |
| 142 | CH3 | | O | CH3 | CH3 | —SO2NHCONH(n-Bu) (R2 = Cl) | |
| 143 | CH3 | | O | C2H5 | CH3 | —NHSO2NHCO(n-Bu) | |
| 144 | CH3 | | O | C2H5 | C2H5 | —CONHSO2C6H5 | |
| 145 | C2H5 | | O | C2H5 | C2H5 | —SO2NHCOC6H5 | |
| 146 | C2H5 | | O | C2H5 | CH3 | —SO2NHCO(n-C5H11) | |
| 147 | C2H5 | | O | C2H5 | CH3 | —SO2NHCO(cy-C3H5) | |
| 148 | C2H5 | | O | C2H5 | CH3 | —SO2NHCOCH2Ph | |
| 149 | —CH3CH2CH=CH2 | | O | C2H5 | CH3 | —NHSO2NHCO(i-C4H9) | |
| 150 | —CH3CH2CH=CH2 | | O | CH3 | CH3 | —NHSO2NHCO(n-gu) | |
| 151 | —CH3CH2CH=CH2 | | O | CH3 | CH3 | —NHSO2NHCO(n-C5H11) | |
| 152 | —CH3CH2CH=CH2 | | O | CH3 | CH3 | —NHSO2NHCO(cy-C3H5) | |
| 153 | C2H5 | | O | CH3 | CH3 | —NHSO2NHCOCH2Ph | |
| 154 | C2H5 | | O | CH3 | CH3 | —SO2NHCO(4Cl—C6H4) | |
| 155 | C2H5 | | O | C2H5 | CH3 | —SO2NHCO(n-C5H11) (R3 = n-Pr) | |
| 156 | C2H5 | | O | C2H5 | CH3 | —SO2NHCO(n-C5H11) (R2 = CH3) | |
| 157 | C2H5 | | O | C2H5 | CH3 | —NHSO2NHCO(n-C5H11) (R3 = n-Pr) | |

TABLE 1-continued

[Structure: imidazoline/imidazolidine ring with R6, R7, R8, R9, R10 substituents, N-CH2 linked to biphenyl with H (or R2), R14, and H (or R3) positions]

| Ex. | R⁶ | R⁷ | R⁸ | R⁹ | R¹⁰ | R¹⁴ | M.S. (M⁺ + H) |
|---|---|---|---|---|---|---|---|
| 158 | C₂H₅ | | O | C₂H₅ | CH₃ | —NHSO₂NHCO(n-Bu) (R² = Cl) | |
| 159 | n-Pr | | O | —(CH₂)₅— | | —SO₂NHCOCF₃ | |
| 160 | n-Pr | | O | —(CH₂)₄— | | —SO₂NHCO(n-C₅H₁₁) (R² = Cl, R³ = n-Pr) | |
| 161 | n-Pr | | O | —(CH₂)₂— | | —NHSO₂NHCO(i-C₅H₁₁) (R² = F, R³ = n-Pr) | |
| 162 | n-Pr | | O | cy-Pr | cy-Pr | —NHSO₂NHCO(n-Bu) (R² = CH₃) | |
| 163 | n-Pr | C(C₆H₅) | (CH₃) | | S | 1H-Tetrazol-5-yl | |
| 164 | n-Pr | C(C₆H₅) | (CH₃) | | O | —CONHSO₂C₆H₅ | |
| 165 | n-Pr | C(C₆H₅) | (CH₃) | | O | —SO₂NHCOC₆H₅ | |
| 166 | n-Pr | C(C₆H₅) | (CH₃) | | O | —SO₂NHCO(n-C₅H₁₁) | |
| 167 | n-Pr | C(C₆H₅) | (CH₃) | | O | —SO₂NHCO(cy-C₃H₅) | |
| 168 | n-Pr | C(C₆H₅) | (CH₃) | | O | —SO₂NHCOCH₂Ph | |
| 169 | n-Pr | C(C₆H₅) | (CH₃) | | O | —NHSO₂NHCO(i-C₄H₉) | |
| 170 | n-Bu | C(C₆H₅) | (CH₃) | | O | —NHSO₂NHCO(n-Bu) | |
| 171 | n-Pr | C(C₆H₅) | (CH₃) | | O | —NHSO₂NHCO(n-C₅H₁₁) | |
| 172 | C₂H₃ | C(C₆H₅) | (CH₃) | | O | —NHSO₂NHCO(cy-C₃H₅) | |
| 173 | n-Bu | C(C₆H₅) | (CH₃) | | O | —NHSO₂NHCOCH₂Ph | |
| 174 | Ph | C(C₆H₅) | (CH₃) | | O | —SO₂NHCO(4Cl—C₆H₄) | |
| 175 | pF—Ph | C(C₆H₅) | (CH₃) | | O | —SO₂NHCO(n-C₅H₁₁) (R³ = n-Pr) | |
| 176 | n-Pr | C(C₆H₅) | (CH₃) | | O | —SO₂NHCO(n-C₅H₁₁) (R² = CH₃) | |
| 177 | n-Pr | C(C₆H₅) | (CH₃) | | O | —NHSO₂NHCO(n-C₅H₁₁) (R³ = n-Pr) | |
| 178 | n-Pr | C(C₆H₅) | (CH₃) | | O | —NHSO₂NHCO(n-Bu) (R² = Cl) | |
| 179 | n-Pr | CH₃ | CH₃ | | N | —SO₂NHCOCF₃ | |
| 180 | CH₃ | CH₃ | CH₃ | | N | —SO₂NHCO(n-C₅H₁₁) (R² = Cl, R³ = n-Pr) | |
| 181 | Ph | CH₃ | CH₃ | | N | —NHSO₂NHCO(i-C₅H₁₁) (R² = F, R³ = n-Pr) | |
| 182 | pF—Ph | CH₃ | CH₃ | | N | —SO₂NHCONH(n-Bu) (R² = Cl) | |
| 183 | n-Pr | C₂H₅ | C₂H₅ | | N | 1H-Tetrazol-5-yl | |
| 184 | n-Pr | C₂H₅ | CH₃ | | N | —SO₂NHCO(4Cl—C₆H₄) | |
| 185 | n-Pr | CF₃ | CF₃ | | N | —SO₂NHCO(n-C₅H₁₁) (R² = CH₃) | |
| 186 | n-Bu | CH₃ | CH₃ | | N | —NHSO₂NHCO(n-C₅H₁₁) (R³ = n-Pr) | |
| 187 | n-Pr | CH₃ | CH₃ | | N | 1H-Tetrazol-5-yl | |
| 188 | n-Pr | CF₃ | CF₃ | | N | —SO₂NHCO(4Cl—C₆H₄) | |
| 189 | n-Pr | —(CH₂)₂— | | | N | —SO₂NHCO(n-C₅H₁₁) (R² = CH₃) | |
| 190 | n-Pr | —(CH₂)₂— | | | N | —NHSO₂NHCO(n-C₅H₁₁) | |
| 191 | n-Pr | C(C₆H₅)₂ | | | S | 1H-Tetrazol-5-yl | |
| 192 | n-Pr | C(C₆H₅)₂ | | | S | 1H-Tetrazol-5-yl | |
| 193 | n-Pr | C(C₆H₅)₂ | | | N | 1H-Tetrazol-5-yl | |
| 194 | n-Pr | C(C₆H₅)₂ | | | O | —CONHSO₂C₆H₅ | |
| 195 | n-Pr | C(C₆H₅)₂ | | | O | —SO₂NHCOC₆H₅ | |
| 196 | n-Pr | C(C₆H₅)₂ | | | O | —SO₂NHCO(n-C₅H₁₁) | |
| 197 | n-Pr | C(C₆H₅)₂ | | | O | —SO₂NHCO(cy-C₃H₅) | |
| 198 | n-Pr | C(C₆H₅)₂ | | | O | —SO₂NHCOCH₂Ph | |
| 199 | n-Pr | C(C₆H₅)₂ | | | O | —NHSO₂NHCO(i-C₄H₉) | |
| 200 | n-Bu | C(C₆H₅)₂ | | | O | —NHSO₂NHCO(n-Bu) | |
| 201 | n-Pr | C(C₆H₅)₂ | | | O | —NHSO₂NHCO(n-C₅H₁₁) | |
| 202 | C₂H₃ | C(C₆H₅)₂ | | | O | —NHSO₂NHCO(cy-C₃H₅) | |
| 203 | Ph | C(C₆H₅)₂ | | | O | —SO₂NHCO(4Cl—C₆H₄) | |
| 204 | pF—Ph | C(C₆H₅)₂ | | | O | —SO₂NHCO(n-C₅H₁₁) (R³ = n-Pr) | |

TABLE 1-continued

| Ex. | $R^6$ | $R^7$ | $R^8$ | $R^9$ | $R^{10}$ | $R^{14}$ | M.S. ($M^+ + H$) |
|---|---|---|---|---|---|---|---|
| 205 | n-Pr | $C(C_6H_5)_2$ | | O | | —NHSO$_2$NHCO(n-Bu) ($R^2$ = CH$_3$) | |
| 206 | n-Pr | $C(C_6H_5)_2$ | | O | | —SO$_2$NHCO(n-C$_5$H$_{11}$) ($R^2$ = CH$_3$) | |
| 207 | n-Pr | $C(C_6H_5)_2$ | | O | | —NHSO$_2$NHCO(n-C$_5$H$_{11}$) ($R^3$ = n-Pr) | |
| 208 | n-Pr | $C(C_6H_5)_2$ | (CH$_3$) | O | | —NHSO$_2$NHCO(n-Bu) ($R^2$ = Cl) | |
| 209 | n-Bu | (CH$_2$)$_3$— | | N | | —NHSO$_2$NHCOCH$_2$Ph | |
| 210 | Ph | (CH$_2$)$_4$— | | N | | —SO$_2$NHCO(4Cl—C$_6$H$_4$) | |
| 211 | pF—Ph | (CH$_2$)$_4$— | | N | | —SO$_2$NHCO(n-C$_5$H$_{11}$) ($R^3$ = n-Pr) | |
| 212 | n-Pr | (CH$_2$)$_4$— | | N | | —NHSO$_2$NHCO(n-Bu) ($R^2$ = CH$_3$) | |
| 213 | n-Pr | (CH$_2$)$_5$— | | N | | —SO$_2$NHCO(n-C$_5$H$_{11}$) ($R^2$ = CH$_3$) | |
| 214 | n-Pr | (CH$_2$)$_5$ | | N | | —NHSO$_2$NHCO(n-C$_5$H$_{11}$) ($R^3$ = n-Pr) | |
| 215 | n-Bu | (CH$_2$)$_4$ | | N | | —NHSO$_2$NHCO(n-Bu) ($R^2$ = CH$_3$) | |
| 216 | n-Pr | CH$_3$ | —CH$_2$-(indol-3-yl) | O | | 1H-Tetrazol-5-yl | |
| 217 | n-Pr | CH$_3$ | —CH$_2$-(indol-3-yl) | O | | —SO$_2$NHCO(n-C$_5$H$_{11}$) ($R^2$ = CH$_3$) | |
| 218 | n-Pr | H | —CH$_2$-(indol-3-yl) | O | | 1H-Tetrazol-5-yl | |
| 219 | n-Pr | H | —CH$_2$-(indol-3-yl) | O | | —SO$_2$NHCO(n-C$_5$H$_{11}$) ($R^2$ = CH$_3$) | |
| 220 | n-Pr | H | CH$_2$COOH | O | | 1H-Tetrazol-5-yl | |
| 221 | n-Pr | H | CH$_2$COOH | O | | —NHSO$_2$NHCO(n-C$_5$H$_{11}$) ($R^3$ = n-Pr) | |
| 222 | n-Pr | H | CH$_2$COOH | O | | —SO$_2$NHCO(cy-C$_3$H$_5$) | |
| 223 | n-Pr | H | CH$_2$COOH | O | | —NHSO$_2$NHCO(n-Bu) ($R^2$ = CH$_3$) | |
| 224 | n-Pr | CH$_3$ | CH$_2$COOH | O | | —NHSO$_2$NHCO(n-Bu) ($R^2$ = CH$_3$) | |

TABLE 1-continued

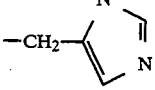

| Ex. | R6 | R7 | R8 | R9 | R10 | R14 | M.S. (M+ + H) |
|---|---|---|---|---|---|---|---|
| 225 | n-Pr | H | —CH2-(imidazolyl) | | O | 1H-Tetrazol-5-yl | |
| 226 | n-Pr | CH3 | —CH2-(imidazolyl) | | O | 1H-Tetrazol-5-yl | |
| 227 | n-Pr | H | —CH2-(imidazolyl) | | O | —NHSO2NHCO(n-C5H11) (R2 = CH3) | |
| 228 | n-Pr | CH3 | —CH2-(imidazolyl) | | O | —NHSO2NHCO(n-C5H11) (R2 = CH3) | |
| 229 | n-Pr | H | —CH2-(imidazolyl) | | O | —NHSO2NHCO(n-C5H11) (R3 = n-Pr) | |
| 230 | n-Pr | CH3 | —CH2-(imidazolyl) | | O | —NHSO2NHCO(n-C5H11) (R3 = n-Pr) | |
| 231 | n-Pr | O | CH3 | CH3 | CH3 | —SO2NHCOO(i-C4H9) | |
| 232 | n-Pr | O | CH3 | CH3 | CH3 | —SO2NHCOO(n-C4H9) | |
| 233 | n-Pr | O | CH3 | CH3 | CH3 | —SO2NHCOO(n-C5H11) | |
| 234 | n-Pr | O | CH3 | CH3 | CH3 | —SO2NHCOO(i-C5H11) | |
| 235 | n-Pr | O | CH3 | CH3 (R2 = CH3) | | —SO2NHCOO(n-C5H11) | |
| 236 | n-Pr | O | CH3 | CH3 (R2 = CH3) | | —SO2NHCOO(n-C4H0) | |
| 237 | n-Pr | O | CH3 | CH3 (R2 = CH3) | | —SO2NHCOO(i-C5H11) | |
| 238 | n-Pr | O | CH3 | CH3 (R2 = CH3) | | —SO2NHCOO(cy-C3H5) | |
| 239 | n-Pr | O | CH3 | CH3 (R2 = CH3) | | —SO2NHCOOCH2C6H5 | |
| 240 | n-Pr | | O | CH3 | CH3 | —SO2NHCOO(n-C4H9) (R2 = Cl) | |
| 241 | n-Pr | | O | CH3 | CH3 | —SO2NHCOO(n-C5H11) (R2 = Cl) | |
| 242 | n-Pr | | O | CH3 | CH3 | —SO2NHCOO(i-C5H11) (R2 = Cl) | |
| 243 | n-Pr | | O | CH3 | CH3 | —SO2NHCOO(cy-C3H5) (R2 = Cl) | |
| 244 | n-Pr | | O | CH3 | CH3 | —SO2NHCOOCH2C6H5 (R2 = Cl) | |
| 245 | n-Pr | | O | CH3 | CH3 | —SO2NHCOO(n-C4H9) (R2 = F) | |

TABLE 1-continued

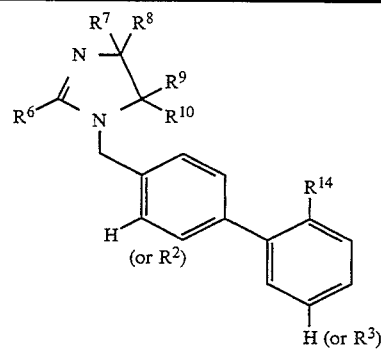

| Ex. | $R^6$ | $R^7$ | $R^8$ | $R^9$ | $R^{10}$ | $R^{14}$ | M.S. ($M^+ + H$) |
|---|---|---|---|---|---|---|---|
| 246 | n-Pr | | O | $CH_3$ | $CH_3$ | $-SO_2NHCOO(n-C_5H_{11})$ ($R^2 = F$) | |
| 247 | n-Pr | | O | $CH_3$ | $CH_3$ | $-SO_2NHCOO(i-C_5H_{11})$ ($R^2 = F$) | |
| 247 | n-Pr | | O | $CH_3$ | $CH_3$ | $-SO_2NHCOO(cy-C_3H_5)$ ($R^2 = F$) | |
| 248 | n-Pr | | O | $CH_3$ | $CH_3$ | $-SO_2NHCOOCH_2C_6H_5$ ($R^2 = F, R^3 = n-C_3H_7$) | |
| 249 | n-Pr | | O | $CH_3$ | $CH_3$ | $-SO_2NHCOO(n-C_4H_9)$ ($R^3 = n-C_3H_7$) | |
| 250 | n-Pr | | O | $CH_3$ | $CH_3$ | $-SO_2NHCOO(n-C_5H_{11})$ ($R^3 = n-C_3H_7$) | |
| 251 | n-Pr | | O | $CH_3$ | $CH_3$ | $-SO_2NHCOO(i-C_5H_{11})$ ($R^3 = n-C_3H_7$) | |
| 252 | n-Pr | | O | $CH_3$ | $CH_3$ | $-SO_2NHCOO(cy-C_3H_5)$ ($R^3 = n-C_3H_7$) | |
| 253 | n-Pr | | O | $CH_3$ | $CH_3$ | $-SO_2NHCOOCH_2C_6H_5$ ($R^3 = n-C_3H_7$) | |
| 254 | n-Pr | | O | $CH_3$ | $CH_3$ | $-SO_2NHCOO(n-C_4H_9)$ ($R^2 = Cl, R^3 = n-C_3H_7$) | |
| 255 | n-Pr | | O | $CH_3$ | $CH_3$ | $-SO_2NHCOO(n-C_5H_{11})$ ($R^2 = F, R^3 = n-C_3H_7$) | |
| 256 | n-Pr | | O | $CH_3$ | $CH_3$ | $-SO_2NHCOO(i-C_5H_{11})$ ($R^2 = Cl, R^3 = n-C_3H_7$) | |
| 257 | n-Pr | | O | $CH_3$ | $CH_3$ | $-SO_2NHCOO(cy-C_3H_5)$ ($R^2 = Cl, R^3 = n-C_3H_7$) | |
| 258 | n-Pr | | O | $CH_3$ | $CH_3$ | $-SO_2NHCOOCH_2C_6H_5$ ($R^2 = F, R^3 = n-C_3H_7$) | |
| 259 | n-Pr | | N | $CH_3$ | $CH_3$ | $-SO_2NHCOO(n-C_5H_{11})$ ($R^3 = n-C_3H_7$) | |
| 260 | n-Pr | | S | $CH_3$ | $CH_3$ | $-SO_2NHCOO(n-C_5H_{11})$ ($R^3 = n-C_3H_7$) | |
| 261 | n-Bu | | S | $CH_3$ | $CH_3$ | $-SO_2NHCOO(n-C_4H_9)$ | |
| 262 | n-Bu | | O | $CH_3$ | $CH_3$ | $-SO_2NHCOO(i-C_4H_9)$ | |
| 263 | n-Bu | | O | $CH_3$ | $CH_3$ | $-SO_2NHCOO(n-C_4H_9)$ | |
| 264 | n-Bu | | O | $CH_3$ | $CH_3$ | $-SO_2NHCOO(n-C_5H_{11})$ | |
| 265 | n-Bu | | O | $CH_3$ | $CH_3$ | $-SO_2NHCOO(cy-C_3H_5)$ | |
| 266 | n-Bu | | O | $CH_3$ | $CH_3$ | $-SO_2NHCOOCH_2Ph$ ($R^3 = n-C_3H_7$) | |
| 267 | n-Bu | | O | $CH_3$ | $CH_3$ | $-SO_2NHCOO(n-C_5H_{11})$ ($R^3 = n-C_3H_7$) | |
| 268 | n-Bu | | O | $CH_3$ | $CH_3$ | $-SO_2NHCOO(n-C_4H_9)$ ($R^2 = Cl$) | |
| 269 | n-Bu | | O | $CH_3$ | $CH_3$ | $-SO_2NHCOO(i-C_5H_{11})$ ($R^2 = F, R^3 = n-C_3H_7$) | |
| 270 | n-Pr | | S | $CH_3$ | $CH_3$ | $-SO_2NHCOO(n-C_4H_9)$ | |
| 271 | n-Pr | | O | $C_2H_5$ | $CH_3$ | $-SO_2NHCOO(i-C_4H_9)$ | |
| 272 | n-Pr | | O | $C_2H_5$ | $CH_3$ | $-SO_2NHCOO(n-C_4H_9)$ | |
| 273 | n-Pr | | O | $C_2H_5$ | $CH_3$ | $-SO_2NHCOO(n-C_5H_{11})$ | |
| 274 | n-Bu | | O | $C_2H_5$ | $CH_3$ | $-SO_2NHCOO(cy-C_3H_5)$ | |
| 275 | n-Bu | | O | $C_2H_5$ | $CH_3$ | $-SO_2NHCOOCH_2Ph$ | |
| 276 | n-Bu | | O | $C_2H_5$ | $CH_3$ | $-SO_2NHCOO(n-C_5H_{11})$ ($R^3 = n-C_3H_7$) | |
| 277 | n-Bu | | O | $C_2H_5$ | $CH_3$ | $-SO_2NHCOO(n-C_4H_9)$ ($R^2 = Cl$) | |
| 278 | n-Bu | | O | $C_2H_5$ | $CH_3$ | $-SO_2NHCOO(i-C_5H_{11})$ ($R^2 = F, R^3 = n-C_3H_7$) | |
| 279 | n-Bu | | O | $CF_3$ | $CF_3$ | $-SO_2NHCOO(i-C_4H_9)$ | |
| 280 | n-Bu | | O | $C_2H_5$ | $C_2H_5$ | $-SO_2NHCOO(n-C_4H_9)$ | |
| 281 | n-Pr | | O | $CF_3$ | $CF_3$ | $-SO_2NHCOO(n-C_5H_{11})$ | |
| 282 | n-Pr | | O | $CF_3$ | $CF_3$ | $-SO_2NHCOO(cy-C_3H_5)$ | |
| 283 | n-Bu | | O | $CF_3$ | $CF_3$ | $-SO_2NHCOOCH_2Ph$ | |

TABLE 1-continued

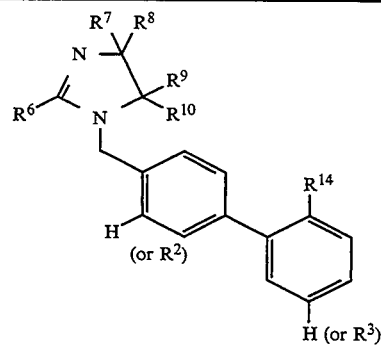

| Ex. | R6 | R7 | R8 | R9 | R10 | R14 | M.S. (M+ + H) |
|---|---|---|---|---|---|---|---|
| 284 | pF—Ph | | O | CH3 | CH3 | —SO2NHCOO(n-C5H11) (R3 = n-C3H7) | |
| 285 | Ph | | O | CH3 | CH3 | —SO2NHCOO(n-C4H9) (R2 = Cl) | |
| 286 | CH3 | | O | CH3 | CH3 | —SO2NHCOO(i-C5H11) (R2 = F, R3 = n-C3H7) | |
| 287 | CH3 | | O | C2H5 | CH3 | —SO2NHCOO(n-C4H9) | |
| 288 | CH3CH2CH=CH2 | | O | C2H5 | CH3 | —SO2NHCOO(i-C4H9) | |
| 289 | CH3CH2CH=CH2 | | O | CH3 | CH3 | —SO2NHCOO(n-C4H9) | |
| 290 | CH3CH2CH=CH2 | | O | CH3 | CH3 | —SO2NHCOO(n-C5H11) | |
| 291 | CH3CH2CH=CH2 | | O | CH3 | CH3 | —SO2NHCOO(cy-C3H5) | |
| 292 | C2H5 | | O | CH3 | CH3 | —SO2NHCOOCH2Ph | |
| 293 | C2H5 | | O | C2H5 | CH3 | —SO2NHCOO(n-C5H11) (R3 = n-C3H7) | |
| 294 | C2H5 | | O | C2H5 | CH3 | —SO2NHCOO(n-C4H9) (R2 = Cl) | |
| 295 | n-Pr | | O | —(CH2)2— | | —SO2NHCOO(i-C5H11) (R2 = F, R3 = n-C3H7) | |
| 296 | n-Pr | | O | cy-Pr | cy-Pr | —SO2NHCOO(n-C4H9) (R2 = CH3) | |
| 297 | n-Pr | C(C6H5) | (CH3) | | O | —SO2NHCOO(i-C4H9) | |
| 298 | n-Bu | C(C6H5) | (CH3) | | O | —SO2NHCOO(n-C4H9) | |
| 299 | n-Pr | C(C6H5) | (CH3) | | O | —SO2NHCOO(n-C5H11) | |
| 300 | C2H3 | C(C6H5) | (CH3) | | O | —SO2NHCOO(cy-C3H5) | |
| 301 | n-Bu | C(C6H5) | (CH3) | | O | —SO2NHCOOCH2Ph | |
| 302 | n-Pr | C(C6H5) | (CH3) | | O | —SO2NHCOO(n-C5H11) (R3 = n-C3H7) | |
| 303 | n-Pr | C(C6H5) | (CH3) | | O | —SO2NHCOO(n-C4H9) (R2 = Cl) | |
| 304 | Ph | CH3 | CH3 | | N | —SO2NHCOO(i-C5H11) (R2 = F, R3 = n-C3H7) | |
| 305 | n-Bu | CH3 | CH3 | | N | —SO2NHCOO(n-C5H11) (R3 = n-C3H7) | |
| 306 | n-Pr | —(CH2)2— | | | N | —SO2NHCOO(n-C5H11) | |
| 307 | n-Pr | C(C6H5)2 | | | O | —SO2NHCOO(i-C4H9) | |
| 308 | n-Bu | C(C6H5)2 | | | O | —SO2NHCOO(n-C4H9) | |
| 309 | n-Pr | C(C6H5)2 | | | O | —SO2NHCOO (n-C5H11) | |
| 310 | C2H3 | C(C6H5)2 | | | O | —SO2NHCOO(cy-C3H5) | |
| 311 | n-Pr | C(C6H5)2 | | | O | —SO2NHCOO(n-C4H9) (R2 = CH3) | |
| 312 | n-Pr | C(C6H5)2 | | | O | —SO2NHCO(n-C5H11) (R2 = CH3) | |
| 313 | n-Pr | C(C6H5)2 | | | O | —SO2NHCOO(n-C5H11) (R3 = n-C3H7) | |
| 314 | n-Pr | C(C6H5)2 | (CH3) | | O | —SO2NHCOO(n-C4H9) (R2 = Cl) | |
| 315 | n-Bu | —(CH2)3— | | | N | —SO2NHCOOCH2Ph | |
| 316 | n-Pr | —(CH2)4— | | | N | —SO2NHCOO(n-C4H9) (R2 = CH3) | |
| 317 | n-Pr | —(CH2)5— | | | N | —SO2NHCOO(n-C5H11) (R3 = n-C3H7) | |
| 318 | n-Bu | —(CH2)4— | | | N | —SO2NHCOO(n-C4H9) (R2 = CH3) | |
| 319 | n-Pr | H | CH2COOH | | O | —SO2NHCOO(n-C5H11) (R3 = n-C3H7) | |
| 320 | n-Pr | H | CH2COOH | | O | —SO2NHCOO(n-C4H9) (R2 = CH3) | |
| 321 | n-Pr | CH3 | CH2COOH | | O | —SO2NHCOO(n-C4H9) (R2 = CH3) | |

TABLE 1-continued

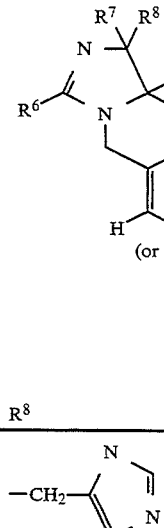

| Ex. | R⁶ | R⁷ | R⁸ | R⁹ | R¹⁰ | R¹⁴ | M.S. (M⁺ + H) |
|---|---|---|---|---|---|---|---|
| 322 | n-Pr | H— | 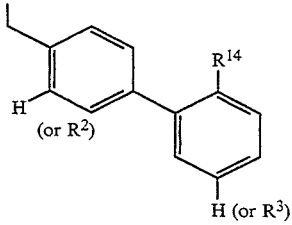 | | O | —SO₂NHCOO(n-C₅H₁₁) (R² = CH₃) | |
| 323 | n-Pr | CH₃ | 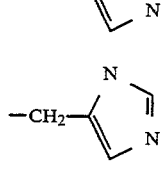 | | O | —SO₂NHCOO(n-C₅H₁₁) (R² = CH₃) | |
| 324 | n-Pr | H— | 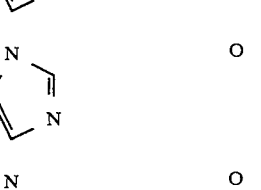 | | O | —SO₂NHCOO(n-C₅H₁₁) (R³ = n-C₃H₇) | |
| 325 | n-Pr | CH₃ | 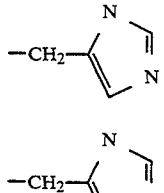 | | O | —SO₂NHCOO(n-C₅H₁₁) (R³ = n-C₃H₇) | |

Utility

Angiotensin II (AII) produces numerous biological responses (e.g., vasoconstriction) through stimulation of its receptors on cell membranes. For the purpose of identifying compounds such as AII antagonists which are capable of interacting with the AII receptor, a ligand-receptor binding assay was utilized for the initial screen. The assay was carried out according to the method described by Chiu, et al., *Receptor*, 1 33, (1990). In brief, aliquots of a freshly prepared particulate fraction of rat adrenal cortex were incubated with 0.05 nM [$^{125}$I] AII and varying concentrations of potential AII antagonists in a Tris buffer. After a 1 h incubation the reaction was terminated by addition of cold assay buffer. The bound and free radioactivity were rapidly separated through glass-fiber filters, and the trapped radioactivity was quantitated by scintillation counting. The inhibitory concentration (IC$_{50}$) of potential AII antagonists which gives 50% displacement of the total specifically bound [$^{125}$I] AII is presented as a measure of the affinity of such compound for the AII receptor.

Using the assay method described above, the compounds of this invention are found to exhibit an activity of at least IC$_{50}$<10 micromolar, thereby demonstrating and confirming the activity of these compounds as effective AII antagonists.

The potential antihypertensive effects of the compounds of this invention may be demonstrated by administering the compounds to awake rats made hypertensive by ligation of the left renal artery [Cangiano et at., *J. Pharmacol. Exp. Ther.*, 1979, 208, 310]. This procedure increases blood pressure by increasing renin-Production with consequent elevation of AII levels. Compounds are administered intravenously via a cannula in the jugular vein at 10 mg/kg. Arterial blood pressure is continuously measured directly through a carotid artery cannula and recorded using a pressure transducer and a polygraph. Blood pressure levels after treatment are compared to pretreatment levels to determine the antihypertensive effects of the compounds.

Using the in vivo methodology described above, the compounds of this invention are found to exhibit an activity (intravenous) which is 10 mg/kg or less, and/or an activity (oral) which is 100 mg/kg or less, thereby demonstrating and confirming the utility of these compounds as effective agents in lowering blood pressure.

The compounds of the invention are useful in treating hypertension. They are also of value in the management of acute and chronic congestive heart failure and angina. These compounds may also be expected to be useful in the treatment of primary and secondary hyperaldosteronism; renal diseases such as diabetic nephropathy, glomerulonephritis, glomerular sclerosis, nephrotic syndrome, hypertensive nephrosclerosis, end stage renal disease, used in renal transplant therapy, and to treat renovascular hypertension, scleroderma, left ventricular dysfunction, systolic and diastolic dysfunction, diabetic retinopathy and in the management of vascular disorders such as migrate, Raynaud's disease, and as prophylaxis to minimize the atherosclerotic process and neointimal hyperplasia following angioplasty or vascular injury and to retard the onset of type II diabetes. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels and the like. Pharmaceutical formulations prepared to treat intraocular pressure would typically contain about 0.1% to 15% by weight, preferably 0.5% to 2% by weight, of a compound of this invention. For this use, the compounds of this invention may also be used in combination with other medications for the treatment of glaucoma including choline esterase inhibitors such as physostigmine salicylate or demecarium bromide, parasympathomimetic agents such as pilocarpine nitrate, β-adrenergic antagonists such as timolol maleate, adrenergic agonists such as epinephrine and carbonic anhydrase inhibitors such as MK-507.

In the management of hypertension and the clinical conditions noted above, the compounds of this invention may be utilized with a pharmaceutical carrier in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patients weight, special diet that is being followed by a patient, concurrent medication, and other factors which those skilled in the art will recognize, the dosage range will generally be about 1 to 1000 mg per patient per day which can be administered in single or multiple doses. Preferably, the dosage range will be about 5 to 500 mg per patient per day; more preferably about 5 to 300 mg per patient per day.

The compounds of this invention can also be administered in combination with other antihypertensives and/or diuretics. For example, the compounds of this invention can be given in combination with diuretics such as hydrochlorothiazide, chlorothiazide, chlorthalidone, methylclothiazide, furosemide, ethacrynic acid, triamterene, amiloride spironolactone and atriopeptin; calcium channel blockers, such as diltiazem, felodipine, nifedipine, amlodipine, nimodipine, isradipine, nitrendipine and verapamil; β-adrenergic antagonists such as timolol, atenolol, metoprolol, propanolol, nadolol and pindolol; angiotensin converting enzyme inhibitors such as enalapril, lisinopril, captopril, ramipril, quinapril and zofenopril; renin inhibitors such as A-69729, FK 906 and FK 744; a-adrenergic antagonists such as prazosin, doxazosin, and terazosin; sympatholytic agents such as methyldopa, clonidine and guanabenzi atriopeptidase inhibitors (alone or with ANP) such as UK-79300; serotonin antagonists such as ketanserin; A2-adrenosine receptor agonists such as CGS 22492C; potassium channel agonists such as pinacidil and cromakalim; and various other antihypertensive drugs including reserpine, minoxidil, guanethidine, hydralazinc hydrochloride and sodium nitroprusside as well as combinations of the above-named drugs. Combinations useful in the management of congestive heart failure include, in addition, compounds of this invention with cardiac stimulants such as dobutamine and xamoterol and phosphodiesterase inhibitors including amrinone and milrinone.

Typically, the individual daily dosages for these combinations can range from about one-fifth of the minimally recommended clinical dosages to the maximum recommended levels for the entities when they are given singly. To illustrate these combinations, one of the angiotensin II antagonists of this invention effective clinically in the 5-500 milligrams per day range can be effectively combined at levels at the 1.0-500 milligrams per day range with the following compounds at the indicated per day dose range: hydrochlorothiazide (6-100 mg), chlorothiazide (125-500 mg), ethacrynic acid (5-200 mg), amiloride (5-20 mg), furosemide (5-80 mg), propranolol (10-480 mg), timolol maleate (1-20 mg), methyldopa (125-2000 mg), felodipine (1-20 mg), nifedipine (5-120 mg), nitrendipine (5-60 mg), and diltiazem (30-540 mg). In addition, triple drug combinations of hydrochlorothiazide (5-100 mg) plus amiloride (5-20 mg) plus angiotensin II antagonists of this invention (1-500 mg) or hydrochlorothiazide (5-100 mg) plus timolol maleate (5-60 mg) plus an angiotensin II antagonists of this invention (1-500 mg) or hydrochlorothiazide (5-200 mg) and nifedipine (5-60 mg) plus an angiotensin II antagonist of this invention (1-500 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The active ingredient can be administered orally in solid dosage forms, such as capsules, tablets, and powders, or in liquid dosage forms, such as elixirs syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol. The solution is made to volume with water for injection and sterilized.

Suspension

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise in conjunction with another therapeutic agent. When the drugs are administered in physical combination, the dosage form and administration route should be selected for compatibility with both drugs.

What is claimed is:

1. A compound of the formula:

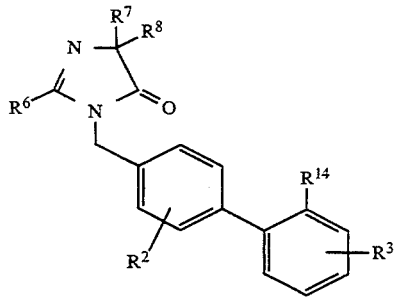

wherein
$R^2$ is
  (a) H,
  (b) halo,
  (c) $C_1$-$C_4$ alkyl,
  (d) $C_1$-$C_4$ alkoxy,
$R^3$ is
  (a) H,
  (b) halo,
  (c) $C_1$-$C_4$ alkyl,
  (d) $C_1$-$C_4$ alkoxy,
  (e) $C_1$-$C_4$ alkoxyalkyl;
$R^6$ is
  (a) $C_1$-$C_7$ alkyl,
  (b) $C_3$-$C_4$ alkenyl,
  (c) $C_3$-$C_4$ alkynyl,
  (d) phenyl, optionally substituted with 1-2 substituents selected from the group of halo, $C_1$-$C_4$ alkyl, $C_1$-$C_4$ alkoxy, nitro, amino, hydroxy and benzyloxy;
$R^7$ and $R^8$ taken together are $CR^{11}R^{12}$;
$R^{11}$ and $R^{12}$ are independently
  (a) H,
  (b) $C_1$-$C_6$ alkyl,
  (c) phenyl,
  (d) benzyl,
$R^{14}$ is
  (a) —$CO_2H$,
  (b) —$CONHSO_2R^{24}$,
  (c) —$NHCONHSO_2R^{24}$,
  (d) —$NHSO_2R^{24}$,
  (e) —$SO_2NHR^{23}$,
  (f) —$SO_2NHCONHR^{23}$, (g) 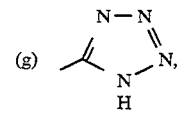

(h) —$NHSO_2NHCOR^{24}$,
  (i) —$SO_2NHCOR^{24}$;
$R^{23}$ is
  (a) H,
  (b) $C_1$-$C_5$ alkyl,
  (c) aryl,
  (d) —$CH_2$-aryl, wherein aryl is phenyl optionally substituted with 1-2 substituents selected from the group of halo, $C_1$-$C_4$ alkyl, $C_1$-$C_4$ alkoxy, nitro, amino, hydroxy and benzyloxy;
$R^{24}$ is
  (a) aryl, where aryl is as defined above,
  (b) $C_3$-$C_7$ cycloalkyl,
  (c) $C_1$-$C_4$ perfluoroalkyl,
  (d) $C_1$-$C_4$ alkyl optionally substituted with a substituent selected from the group consisting of aryl as defined above, —OH, —SH, $C_1$-$C_4$ alkyl, $C_1$-$C_4$ alkoxy, $C_1$-$C_4$ alkylthio, —$CF_3$, halo, —$NO_2$, —$CO_2H$, —$CO_2CH_3$, —$CO_2$—benzyl, —$NH_2$, $C_1$-$C_4$ alkylamino, $C_1$-$C_4$ dialkylamino, or —$PO_3H_2$,
  (e) $C_1$-$C_4$ alkoxy optionally substituted with a substituent selected from the group consisting of aryl as defined above, —OH, —SH, $C_1$-$C_4$ alkyl, $C_1$-$C_4$ alkoxy, $C_1$-$C_4$ alkylthio, —$CF_3$, halo, —$NO_2$, —$CO_2H$, —$CO_2CH_3$, —$CO_2$-benzyl, —$NH_2$, $C_1$-$C_4$ alkylamino, $C_1$-$C_4$ dialkylamino, —$PO_3H_2$; or a pharmaceutically acceptable salt thereof.

2. A compound of claim 1 selected from the group consisting of 3,5-Dihydro-5-(1-phenylethylidene)-2-propyl-3-[(2'-(1H-tetrazol-5-yl)(1,1'-biphenyl)-4-yl)methyl]-4H-imidazol-4-one and 4'(3,5-dihydro-5-(1-phenylethylidene)-2-propyl-4H-imidazol-4-one-3-yl-methyl)-3'-methyl(1,1'-biphenyl-2-yl)sulfonyl carbamic acid n-butyl ester.

3. A pharmaceutical composition comprising a pharmaceutically suitable carrier and a compound of claim 1.

4. A method of treating hypertension in a warm blooded animal comprising administering to an animal in need of such treatment an effective amount of a compound of claim 1.

5. A method of treating congestive heart failure in a warm blooded animal comprising administering to an animal in need of such treatment an effective amount of a compound of claim 1.

* * * * *